US006994700B2

(12) United States Patent
Elkins et al.

(10) Patent No.: US 6,994,700 B2
(45) Date of Patent: Feb. 7, 2006

(54) APPARATUS AND METHOD FOR INSERTING AN INTRA-AORTA CATHETER THROUGH A DELIVERY SHEATH

(75) Inventors: Jeffrey M. Elkins, Novato, CA (US); Harry B. Goodson, Fremont, CA (US); Mark A. Maguire, San Mateo, CA (US); Aurelio Valencia, East Palo Alto, CA (US); Samir R. Patel, Mountain View, CA (US)

(73) Assignee: Flowmedica, Inc., Fremont, CA (US)

( * ) Notice: Subject to any disclaimer, the term of this patent is extended or adjusted under 35 U.S.C. 154(b) by 0 days.

(21) Appl. No.: 11/084,295

(22) Filed: Mar. 18, 2005

(65) Prior Publication Data

US 2005/0245892 A1 Nov. 3, 2005

Related U.S. Application Data

(63) Continuation of application No. PCT/US03/29585, filed on Sep. 22, 2003.

(60) Provisional application No. 60/502,399, filed on Sep. 13, 2003, provisional application No. 60/486,206, filed on Jul. 9, 2003, provisional application No. 60/412,476, filed on Sep. 20, 2002.

(51) Int. Cl.
*A61M 25/01* (2006.01)

(52) U.S. Cl. ........................... 604/528; 604/523

(58) Field of Classification Search ............... 604/500, 604/523, 528, 264, 272, 502, 104
See application file for complete search history.

(56) References Cited

U.S. PATENT DOCUMENTS 1,696,018 A   12/1928  Schellberg
2,499,045 A   2/1950   Walker et al.
3,344,791 A * 10/1967  Foderick ..................... 604/104
3,455,298 A   7/1969   Anstadt
3,516,408 A   6/1970   Montanti
3,667,069 A   6/1972   Blackshear et al.
3,730,186 A   5/1973   Edmunds, Jr. et al.

(Continued)

FOREIGN PATENT DOCUMENTS

DE          43 24 637 A1    3/1995

(Continued)

OTHER PUBLICATIONS

"FDA Form 510(K) on related correspondence for Advanced Equipment Development, Inc.".

(Continued)

*Primary Examiner*—Sharon Kennedy
(74) *Attorney, Agent, or Firm*—Townsend and Townsend and Crew LLP

(57) ABSTRACT

An introducer system delivers therapy locally to a renal system in a patient. A proximal coupler assembly is coupled to an introducer sheath that delivers multiple devices simultaneously into a location within an abdominal aorta associated with first and second renal artery ostia. The coupler assembly has a network of branch lumens arranged to allow for smooth slideable engagement of multiple coupled devices without substantial interference therebetween. A first branch lumen typically introduces a percutaneous translumenal interventional device such as an angiography or guiding catheter into the introducer sheath and is substantially aligned with a longitudinal axis of the sheath. One or more other branch lumen are off-axis from the longitudinal axis by about 30 degrees or less and introduce components of a bilateral renal delivery assembly into the introducer sheath in conjunction with the other device. Novel insertion devices are provided to coordinate the coupling of the multiple devices.

5 Claims, 22 Drawing Sheets

U.S. PATENT DOCUMENTS

| | | |
|---|---|---|
| 3,791,374 A | 2/1974 | Guarino |
| 3,970,090 A * | 7/1976 | Loiacono .................... 604/104 |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,449,532 A * | 5/1984 | Storz ........................ 606/191 |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,784,639 A * | 11/1988 | Patel ........................ 604/508 |
| 4,817,586 A | 4/1989 | Wampler |
| 4,834,707 A | 5/1989 | Evans |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | Fenton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,493 A * | 10/1994 | Schweich et al. ........... 604/264 |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,397,307 A | 3/1995 | Goodin |
| 5,411,479 A | 5/1995 | Bodden |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A | 4/1996 | Anaya Fernandez de Lomana |
| 5,509,428 A | 4/1996 | Dunlop |
| 5,536,250 A | 7/1996 | Klein et al. |
| 5,558,617 A | 9/1996 | Heilman et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. |
| 5,643,215 A | 7/1997 | Fuhrman et al. |
| 5,702,343 A | 12/1997 | Alferness |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A | 7/2000 | Morejohn et al. |
| 6,117,117 A | 9/2000 | Mauch |
| 6,165,120 A | 12/2000 | Schweich et al. |
| 6,176,852 B1 * | 1/2001 | Ischinger .................... 604/523 |
| 6,287,608 B1 | 9/2001 | Levin et al. |
| 6,387,037 B1 | 5/2002 | Bolling et al. |
| 6,390,969 B1 | 5/2002 | Bolling et al. |
| 6,468,241 B1 | 10/2002 | Gelfand et al. |
| 6,508,787 B2 | 1/2003 | Erbel et al. |
| 6,514,226 B1 | 2/2003 | Levin et al. |
| 6,533,747 B1 | 3/2003 | Polschegg et al. |
| 6,592,567 B1 | 7/2003 | Levin et al. |
| 6,595,959 B1 | 7/2003 | Statienko et al. |
| 6,699,231 B1 | 3/2004 | Sterman et al. |

| | | | |
|---|---|---|---|
| 2001/0031907 A1 | 10/2001 | Downey et al. | |
| 2002/0090388 A1 | 7/2002 | Humes et al. | |
| 2002/0091355 A1 | 7/2002 | Hayden | |
| 2002/0169413 A1 | 11/2002 | Keren et al. | |
| 2003/0069468 A1 | 4/2003 | Bolling et al. | |
| 2003/0100919 A1 | 5/2003 | Hopkins et al. | |
| 2003/0144636 A1 | 7/2003 | Liu | |
| 2003/0153898 A1 | 8/2003 | Schon et al. | |
| 2003/0181856 A1 | 9/2003 | Goldman | |
| 2004/0044302 A1 | 3/2004 | Bernard et al. | |
| 2004/0064089 A1 | 4/2004 | Kesten et al. | |

FOREIGN PATENT DOCUMENTS

| | | |
|---|---|---|
| EP | 0 654 283 A1 | 5/1995 |
| EP | 0 884 064 A2 | 12/1998 |
| GB | 2 239 675 A | 7/1997 |
| WO | WO 97/11737 A1 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/22784 A1 | 5/1999 |
| WO | WO 99/33407 A1 | 7/1999 |
| WO | WO 99/51286 A1 | 10/1999 |
| WO | WO 00/41612 A1 | 7/2000 |
| WO | WO 01/41861 | 6/2001 |
| WO | WO 01/083016 A3 | 11/2001 |
| WO | WO 01/97687 A1 | 12/2001 |
| WO | WO 01/97717 A1 | 12/2001 |
| WO | WO 01/97878 A1 | 12/2001 |
| WO | WO 01/97879 A1 | 12/2001 |

OTHER PUBLICATIONS

Agostoni et al. "Sustained Benefit from Ultrafiltration in Moderate Congestive Heart Failure", *Cardiology* 2001:96 183-189.

Akaba et al., "A Cylinder-Shaped Ballon Catheter for the Management of Dissecting Aneurysms in Acute Stage," *Herz*, vol. 17, No. 6, pp. 390-393, Dec., 1992. Abstract Only.

Aspelin, et al., "Nephrotoxic Effects in High-Risk Patients Undergoing Angiography," *N Engl J Med*, Feb. 2003, vol. 348, No. 6, pp. 491-499.

Bakris et al., "Renal Hemodynamics in Radiocontrast Medium-Induced Renal Dysfunction: A Role for Dopamine-1 Receptors," *Kidney International*, vol. 56 pp. 206-210 (1999).

Beregi, et al., "Doppler Flow Wire Evaluation of Renal Blood Flow Reserve in Hyertenstive Patient With Normal Renal Arteries," *CardioVascular and Interventional Radiology*, vol. 23, pp. 340-346 (2000).

Bergey et al., "Transhepatic Insertion of Vascular Dialysis Catheters in Children: A Safe, Life-Prolonging Procedure," *Pediatr. Radiol.*, vol. 29, No. 1, pp. 42-50, Jan. 1999. Abstract Only.

Bischoff et al., "Modified in Situ Perfusion of the Kidney Using Balloon Catheters," *Fortschr Med* vol. 94, No. 30, pp. 1695-1697, Oct. 21, 1976. Abstract Only.

Canaud et al., "Temporary Vascular Access for Extracorporeal Renal Replacement Therapies in Acute Renal Failure Patients," *Kidney Int. Suppl.*, vol. 66, pp. S142-S150, May, 1998. Abstract Only.

Chatterjee, "Refractory heart failure-drugs and devices", *European Heart Journal*, 2001, 22:2227-2230.

Chu, et al. "Fenoldopam in the Prevention of Contrast Media-Induced Acute Renal Failure," *The Annals of Pharmacotherapy*, 35:1278-1282 (2001).

Cohn, "The Management of Chronic Heart Failure," *The New England Journal of Medicine*, pp. 490-498, Aug. 15, 1996.

Darves, "ASHP: Perioperative Fenoldopam Improves Renal Function During Major Surgery," Retrieved from the Internet [Online]: www.psigroup.com/dg/225C72.htm, Dec. 19, 2002.

Del Greco, "The Kidney in Congestive Heart Failure," *Modern Concepts of Cardiovascular Disease*, Sep. 1975, vol. 44, No. 9, pp. 47-52.

D'Elia et al., "Nephrotoxicity from Angiographic Contrast Material, A Prosepctive Study," *Am J Med*, May 1982, vol. 72, pp. 719-725.

Diaz-Sandoval, et al., "Acetylcysteine to Prevent Angiography-Related Renal Tissue Injury," *The American Journal of Cardiology*, Feb. 1, 2002: vol. 89, pp. 356-358.

Drescher et al., "Prevention of Contrast Medium-Induced Renal Vasospasm by Phosphodiesterase Inhibition," *Invest Radiol* 1998;33:858-862.

Eisenberg et al., "Renal Failure after Major Angiography Can be Avoided with Hydration", *AJR*, May 1981; 136:859-561.

Eisenberg et al., "Renal Failure After Major Angiography," *Am J Med*, Jan. 1980, vol. 68, pp. 43-46.

Eisenberger et al., "Transfemoral Cannulation of the Renal Vessels. Diagnostic and Therapeutic use in Urology," *Urologe* [A], vol. 16, No. 1, pp. 1-5, Jan., 1977. Abstract Only.

Elkayam et al., "Renal Hemodynamic Effects of Vasodilation with Nifedipine and Hydralazine in Patients With Heart Failure," *JACC*, vol. 4, No. 6 (Dec. 1984), pp. 1261-1267.

Elkayam et al., "Renal Vasodilatory Effect of Endothelial Stimulation in Patients with Chronic Congestive Heart Failure," *J Am Coll Cardiol* 1996;28: 176-182.

Fox, "Mechanisms of Contraction," *Human Physiology*, Fourth Edition, Chapter 12, pp. 300-323.

Freeman, et al., "Nephropathy Requiring Dialysis After Percutaneous Coronary Intervention and the Critical role of an Adjusted Contrast Dose," *Am J Cardiol*, vol. 90, (Nov. 15, 2002) pp. 1068-1073.

Garwood et al., "Renal Preservation Strategies for High Risk Patients," *University of Chico School of Medicine*, Cover Page, Table of Contents Page, pp. 1-19, (1998).

Gerlach, et al., "Contrast Medium-Induced Nephrotoxicity: Pathophysiology and Prevention," *Pharmacotherapy*, 2000, 20(5):540-548.

Greco et al., "Atherosclerotic Ischemic Renal Disease," *Am. J. Kidney Dis.*, vol. 29, No. 2, pp. 167-187, Feb., 1997. Abstract Only.

Gruberg, et al., "The Prognostic Implications of Further Renal Function Deterioration Within 48 h of Interventional Coronary in Patients With Pre-existent Chronic Renal Insufficiency," *J Am Coli Cardiol*, 2000, vol. 36 No. 5, pp. 1542-1548.

Halpenny, et al., "The effects of fenoldopam on fenal blood flow and tubular function during aortic cross-clamping in anaesthetized dogs," *Eur J Anaesthesiol*, Aug. 2000;17(8); 491-8 Abstract Only.

Heyman et al.,"Pathophysiology of Radiocontrast Nephropathy, A Role for Medullary Hypoxia," *Invest Radiol*, 1999;34:685-691.

Hobbs, et al., "An Update on Nesiritide for Treatment of Decompensated Heart Failure," *Exp. Opin. Invest. Drugs*, 2001, 10(5):935-942.

Houghton, et al., "Basal and Reserve Renal Artery Blood Flow: Effect of Endothelium-Dependent and Independent Vasoactive Agonists and Radiographci Contrast Medium in Two Patients", *J invas Cardiol* 2000,12:211-215.

Iannone et al., "Effect of Primary Balloon Expandable Renal Artery Stents on Long-Term Patency, Renal Function, and Blood Pressure in Hypertensive and Renal Insufficient Patients with Renal Artery Stenosis," *Cathet. Cardiovasc. Diagn.*, vol. 37, No. 3, pp. 243-250, Mar., 1996. Abstract Only.

Jacobs et al., "Reduced Renal Failure Following Thoracoabdominal Aortic Aneurysm Repair by Selective Perfusion," *Eur. J. Cardiothorac. Surg.*, vol. 14, No. 2, pp. 201-205, Aug., 1998. Abstract Only.

Katsumata et al., "Newly-Developed Catheter for Cardio-Renal Assist During Intraaortic Balloon Counterpulsation," *Kyobu Geka*, vol. 46, No. 9, pp. 767-770, Aug., 1993 Abstract Only.

Kay, et al., Acetylcysteine for Prevention of Acute Deterioration of Renal Function Following Elective Coronary Angiography and Intervention, *JAMA*, vol. 289 No. 5, (Feb. 5, 2003).

Kehrer et al., "Construction and Experimental Application of a Catheter for Selective Arterial Kidney Perfusion in Situ", *Urological Research*, 1985, 13:85-89.

Kim et al., "Fluoroscopic Landmarks for Optimal Visualization of the Proximal Renal Arteries," *JVIR*, 10:37-39 (1999).

Kini et al., "A Protocol for Prevention of Radiographic Contrast Nephropathy During Pecutanous Coronary Intervention," *Catheterization and Cardiovascular Interventions*, 2002, 55:169-173.

Kini, et al., "Managing the High-Risk Patient: Experience with Fenoldopam, a Selective Dopamine Receptor Agonist in Prevention of Radiocontrast Nephropathy During Precutaneous Coronary Intervention," *Rev Cardiovasc Med.* 2001, 2(suppl 1):S19-S25.

Kobayashi et al., "Experimental Study on the Usefulness of the Autoperfusion Balloon Catheter in Maintaining the Blood Supply to the Distal Organs," *Nippon Igaku Hoshasen Gakkai Zasshi*, vol. 52, No. 5, pp. 682-684, May 25, 1992. Abstract Only.

Lass et al., "Cardiovascular and Renal Hemodynamic Effects of Intravenous Infusions of the Selective $DA_1$ Agonist, Fenoldopam, Used Alone or in Combination With Dopamine and Dobutamine", *Circulation* 1988;78:1310-1315.

Levin, Howard et al., "Reversal of Chronic Ventricular Dilation in Patients with End-Stage Cardiomyopathy by Prolonged Mechanical Unloading," *Circulation* vol. 91, No. 11, pp. 2717-2718, Jun. 1, 1995.

Linden et al., "The Nature of the Atrial Receptors Responsible for a Reflex Decrease in Activity in Renal Nerves in the Dog," *The Physiological Society*, pp. 31-40, (1980).

Madyoon, "Clinical Experience with the Use of the Fenoldopam for Prevention of Radiocontrast Hephropathy etc," *Rev Cardiovasc Med.* 2001, 2(suppl 1);S26-S30.

Madyoon, "Use Fenoldopam to Prevent Radiocontrast Nephropathy in High-Risk Patients," *Catheterization and Cardiovascular Interventions*, 2001;53:341-345.

Margulies et al., "Intra-Arterial Atrial Natriuretic Factor (ANF) Attenuates Radiocontrast-Induced Nephropathy in Humans.," *Renal Pathology*, unknown date, pp. 666, Abstract only.

Margulies et al., "Induction and Prevention of Radiocontrast-Induced Nephropathy in Dogs with Heart Failure", *Kidney Int.* 1990; vol. 38:1101-1108.

Masaki et al., "In Situ Perfusion by Retrograde Cannulation of a Tumor Artery for Nephron-Sparing Surgery," *Int. J. Urol*, vol. 2, No. 3, pp. 161-165, Jul., 1995. Abstract Only.

Mason et al., "Renal Dysfunction After Arteriography," *JAMA*, 1985;253:1001-1004.

Mathis et al., "Use of a Guide Catheter as a Temporary Stent During, Microcatheter Intervention," *AJNR Am. J. Neuroradiol*, vol. 19 No. 5, pp. 932-933, May, 1998. Abstract Only.

Mathur, "The Role of the $DA_1$ Receptor Agonist Fenoldopam in the Management of Critically Ill, Transplant, and Hypertensive Patients," *Reviews in Cardiovascular Medicine*, 2003;4(Supp 1):S35-S40.

Mathur, et al., "The Effects Of Fenoldopam, a Selective Dopamine Receptor Agonist, On Renal Hemodynamics in Normotensive Subjects," *Crit Cre Med* Sep. 1999;27(9): 1832-1837, Abstract only.

McCarthy, "Animal Models in Medical Device Development and Qualification," *Charles River Laboratories*, vol. 10(2) 1997.

McCullough et al., "Acute Renal Failure After Coronary Intervention: Incidence, Risk Factors, and Relationship to Mortality," *Am J Med.* 1997;103:368-375.

Mehran, et al., "A Risk Score for Prediction of Contrast Induced nephropathy After Percutaneous Coronary Intervention," Retrieved from the Internet [Online]: www.abstractsonline.com/viewer, Mar. 31, 2003.

Mehran, et al., "Radiocontrast-Induced Acute Renal Failure: Allocations and Outcomes," *Rev Cardiovasc Med* 2001;2 (suppl1):S9-S13.

Middleton, "Ischemic Disease of the Kidney: How and Why to Consider Revascularization," *J. Nephrol.*, vol. 11, No. 3, pp. 123-136, May-Jun., 1998. Abstract Only.

Miller, et al., "Effects of Fenoldopam on Renal Blood Flow and Tubular Function Following Supraerenal Aortic Cross-Clamping," *Ann Vasc Surg*, 2003, Published online Oct. 23, 2003. Abstract Only.

Mintz, et al., "Radiocontrast-Induced Nephropathy and Percutaneous Coronary Intervention," *Expert Opin. Pharmacother.*, 2003; 4(5):639-652.

Mueller, et al., "Prevention of Contrast Media-Associated Nephropathy," *Arch Intern med*, Feb. 2002, vol. 162, pp. 329-336.

Nohria, et al., Medical Management of Advanced Heart Failure, *JAMA*, Feb. 6, 2002; vol. 287, No. 5, pp. 628-640.

Novick, "Atherosclerotic Ischemic Nephropathy. Epidemiology and Clinical Considerations," *Urol. Clin. North Am.*, vol. 21, No. 2, pp. 195-200, May, 1994. Abstract Only.

Paganini, et al., "Severity Scores and Outcomes With Acute Renal Failure in the ICU Setting," *Contrib Nephrol*, 2001; 132: 181-195.

Parfrey et al., "Contrast Material-Induced Renal Failure in Patients with Diabetes Mellitus, Renal Insufficiency, or Both," *N Engl J Med* 1989;320:143-149.

Patel et al., "Intravenous Fenoldopam Infusion in Severe Heart Failure," *Cardiovasc Drugs Ther*, 1993;7:97-101.

Postma et al., "Treatment of Renal Artery Stenosis with Intra-Arterial Stents," *Ned Tijdschr Geneeskd*, vol. 142, No. 39, pp. 2132-2137, Sep. 26, 1998. Abstract Only.

Ramanathan, et al., Ameliorating Contrast-Induced Nephropathy, Journal of Invasive Cardiology, Nov. 2001, Retrieved from the Internet [Online]: www.invasivecardiology.comlfic_20011/jic_200111f6.html.

Rebeiz, et al., "Radiocontrast Nephropathy: a Time for Affirmative Action, *J Invasive Cardiology*," Jan., 2003; vol. 15, No. 1, pp. 23-24.

Rihal, et al., "Incidence and Prognostic Importance of Acute Renal Failure After Percutaneous Coronary Intervention," *Circulation*, (May 14, 2002),105:2259-2264.

Ritchie, et al., "Use of nonionic or Low Osmolar Contrast Agents in Cardiovascular Procedures," Retrieved from the Internet [Online] www.acc.org/clinical/position/72543.htm, Jan. 22, 2003.

Robinson, et al., "Congestive Heart Failure: Targeted Drug Therapy and Invasive Interventions", Retrieved from the Internet [Online] www.speroff.com/articieslTextbook/66_CHF2.htm, printed Sep. 4, 2002.

Rudnick et al., "Nephrotoxicity of Ionic and Noionic Contrast Media in 1196 Patients: A Randomized Trial," *Kidney International*, 1995;47:254-261.

Schwab et al., "Contrast Nephrotoxicity: A Randomized Controlled Trial of a Nonionic and an Ionic Radiographic Contrast Agent," *N Engl J Med*, 1989,320:149-153.

Seiter, H. et al., "Modified T-Catheter and its Use for Transvenous Hypothermic in Situ Perfusion in the Surgical Restoration of the Kidney with Staghorn Calculi," *Z. Urol Nephrol.*, vol. 76, No. 6 pp. 403-406, Jun., 1983. Abstract Only.

Shusterman et al., "Fenoldopam, But Not Nitroprusside, Improves Renal Function in Severely Hypertensive Patients With Impaired Renal Function," *Am J of Medicine*, 95:161-168 (1993).

Solomon et al., "Effects of Saline, Mannitol, and Furosemide on Accute Decreases in Renal Function Induced by Radiocontrast Agents.," *N Engl J Med* 1994; vol. 331 No. 21 pp. 1416-1420.

Stevens et al., "A Prospective Randomized Trial of Prevention Measures in Patients at High Risk for Contrast Nephropathy," *J Am Coli Cardiol*, 1999;33:403-411.

Strick et al., "Direct Measurement of Renal Medullary Blood Flow in the Dog," *Am J. Physiol.* 267 (Regulatory Integrative Compo Physiol. 36): R253-R2259, 1994.

Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298, No. 3 pp. 1154-1160 (2001).

Taliercio et al., "Risks for Renal Dysfunction with Cardiac Angiography," *Annals of Internal Medicine*, 1986;104:501-504.

Thomas et al., "Glomerrular Filtration Dynamics During Renal Vasodilation with Acetylcholine in the Dog.," *Am. J. Physiol.* 244:F606-F611 (1983).

Thomas et al., "Influence of Bradykinin and Papaverine on Renal and Glomerular Hemodynamics in Dogs.," *Renal Physiology*, Basel 5:197-205 (1982).

Tumlin, et al., "Fenoldopam Mesylate Blocks Reductions in Renal Plasma Flow After Radiocontrast Dye Infusion," *Am Heart J* 2002;143:894-903.

UIC College Of Pharmacy, "Is Fenoldopam (Corlopam) Useful for the Prevention Of Contrast Media Associated Nephrotoxicity?", Retrieved from the Internet [Online] www.uic.edu/pharmacy/services/di/fenoldopam.htm, Jan. 2003.

Umrani, et al., "Beneficial Effects Offenoldopam Treatment on Renal Function in Streptozotocin-Induced Diabetic Rats," *Clin Exp Hypertens*, Apr. 2002;24(3):207-19 Abstract Only.

Vari et al., "Induction, Prevention and Mechanisms of Contrast Media-Induced Acute Renal Failure," *Kidney International*, 1988; 33:669-707.

Walker et al., "Use of a Balloon-Tipped Perfusion Catheter for Renal Preservation During Suprarenal Abdominal Aortic Operations," *J. Vasc. Surg.*, vol. 2, No. 2, pp. 337-339, Mar., 1985. Abstract Only.

White et al., "Renal Artery Stent Placement: Utility in Lesions Difficult to Treat with Balloon Angioplasty," *J. Am. Coll. Cardiol.*, vol. 30, No. 6, pp. 1445-1450, Nov. 15, 1997. Abstract Only.

Williams et al., "Design and Testing of a High-FLO2 Autoperfusion Catheter: An Experimental Study," *J. Vasc. Interv. Radiol.*, vol. 3, No. 2, pp. 285-290, May, 1992. Abstract Only.

Zacherl, et al. "Periarterial Papverine Applications Improves Intraoperative Kidney Function During Laparoscopic Donor Nephrectomy", *Journal of Surgical Research* 103:268-271 (2002).

* cited by examiner

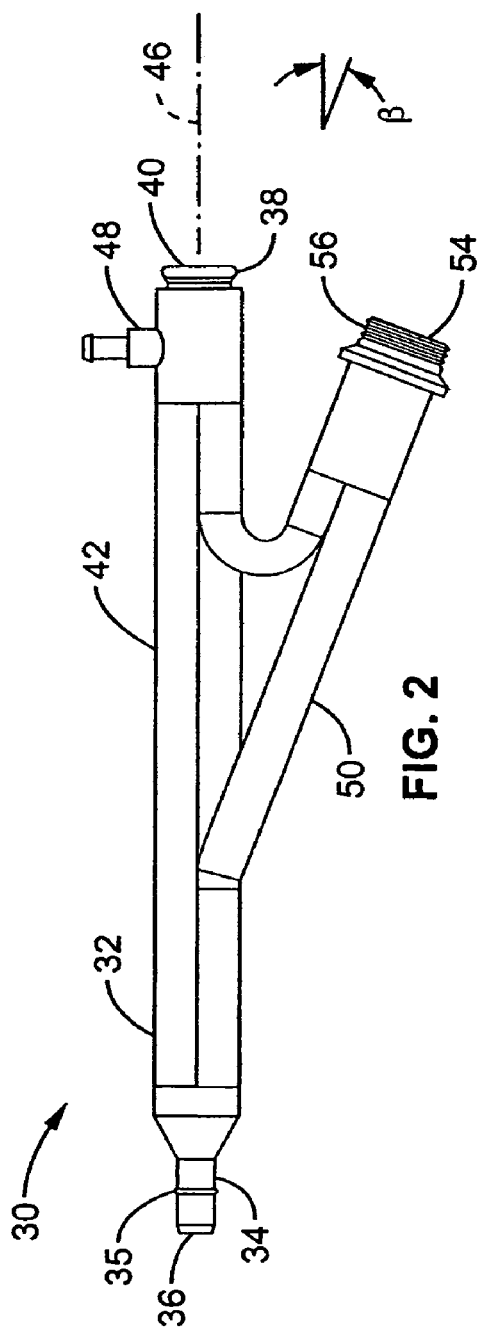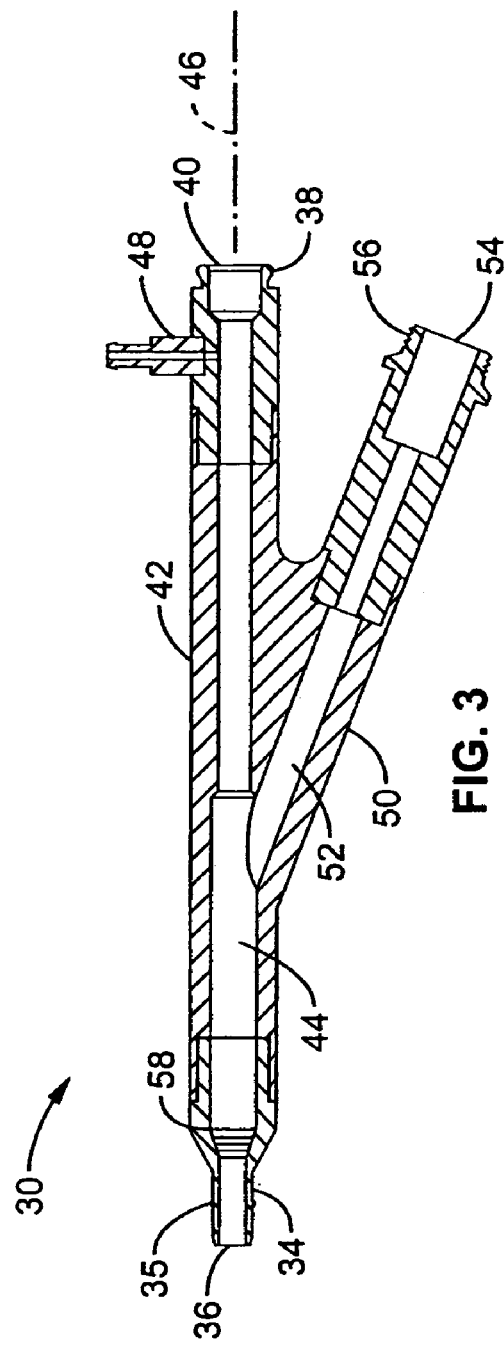

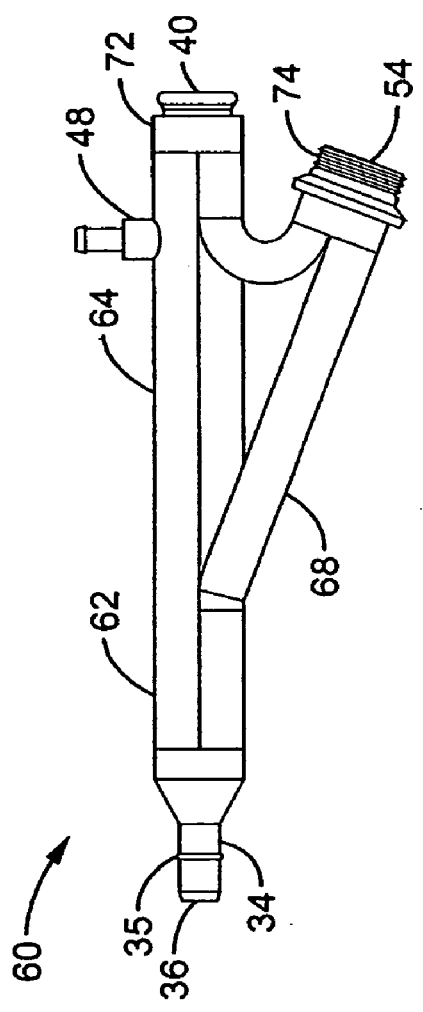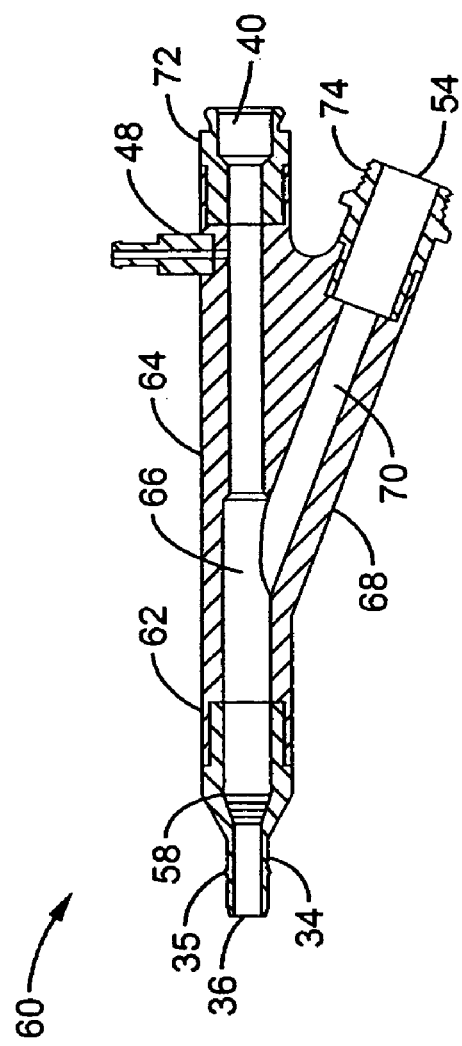

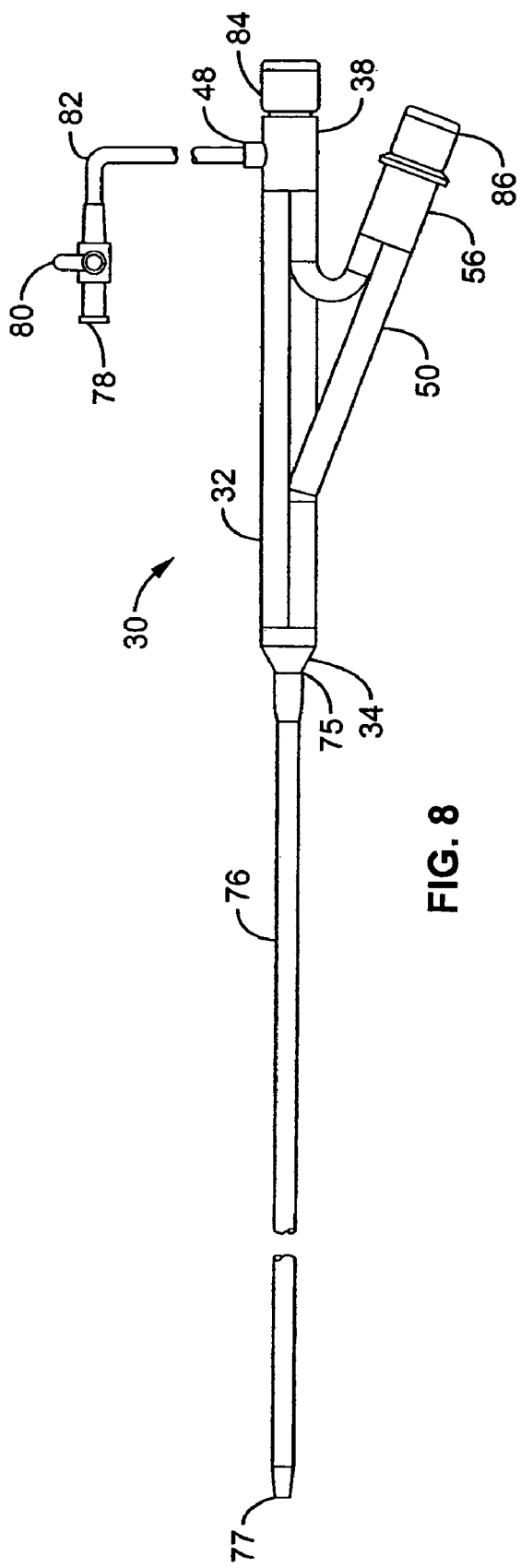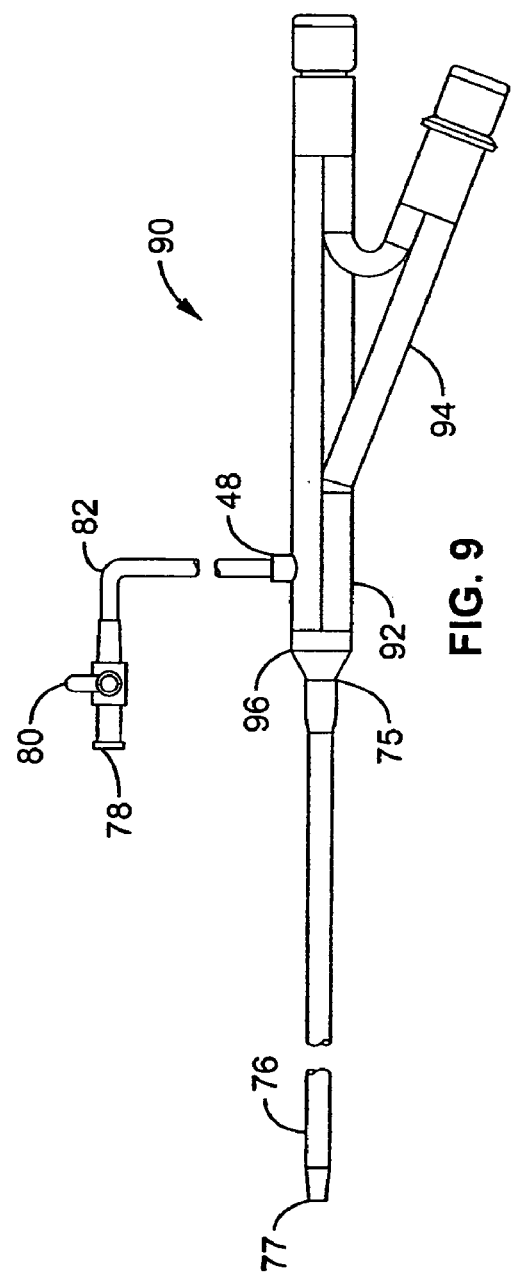
FIG. 8
FIG. 9

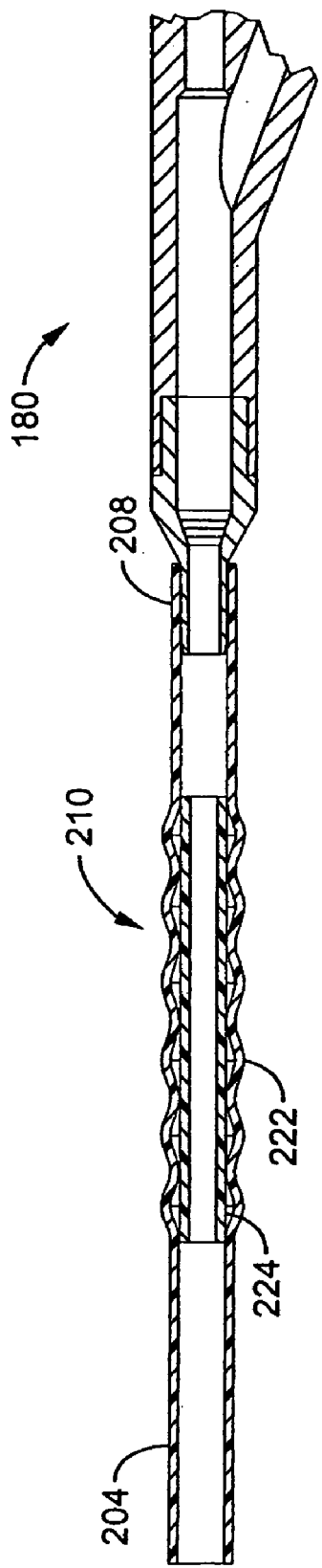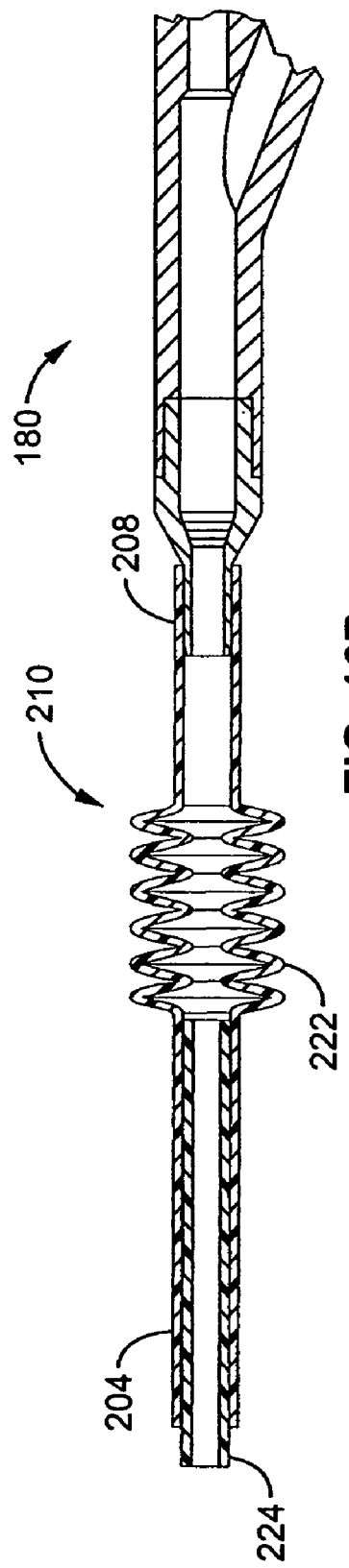
FIG. 16A
FIG. 16B

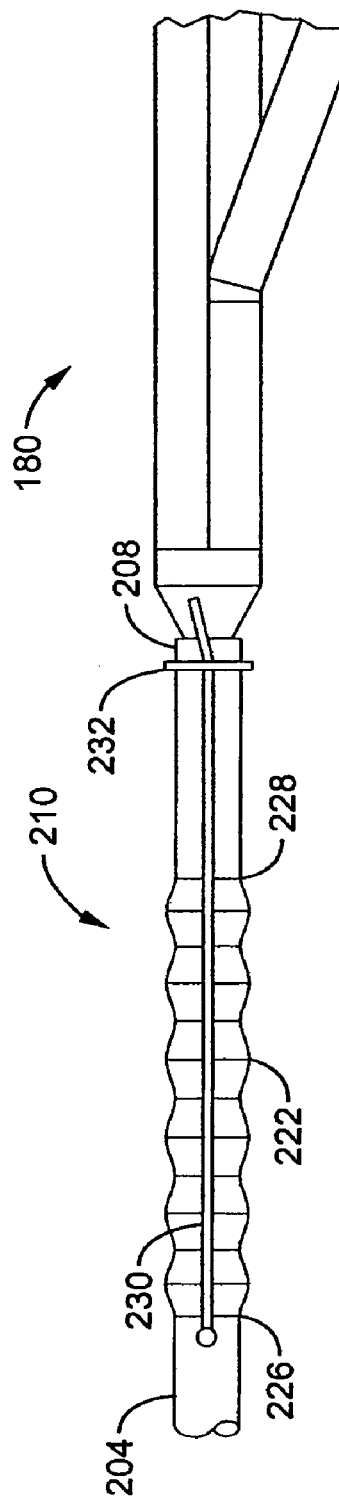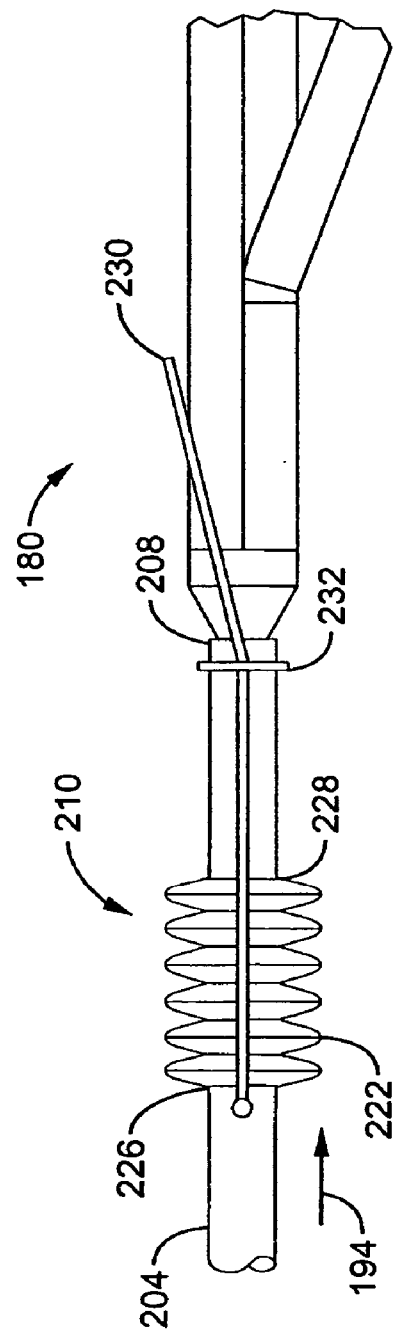
FIG. 17A
FIG. 17B

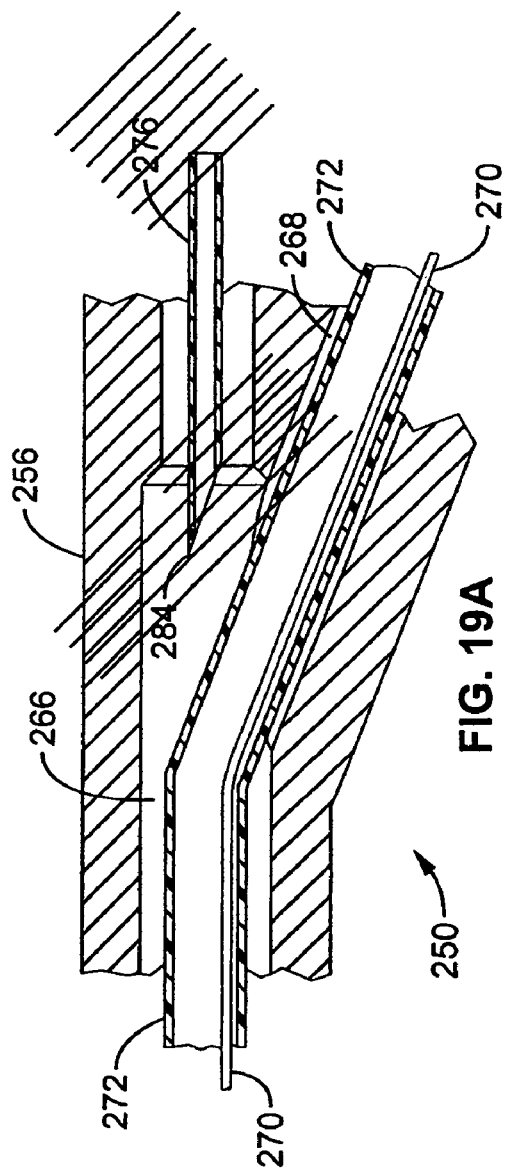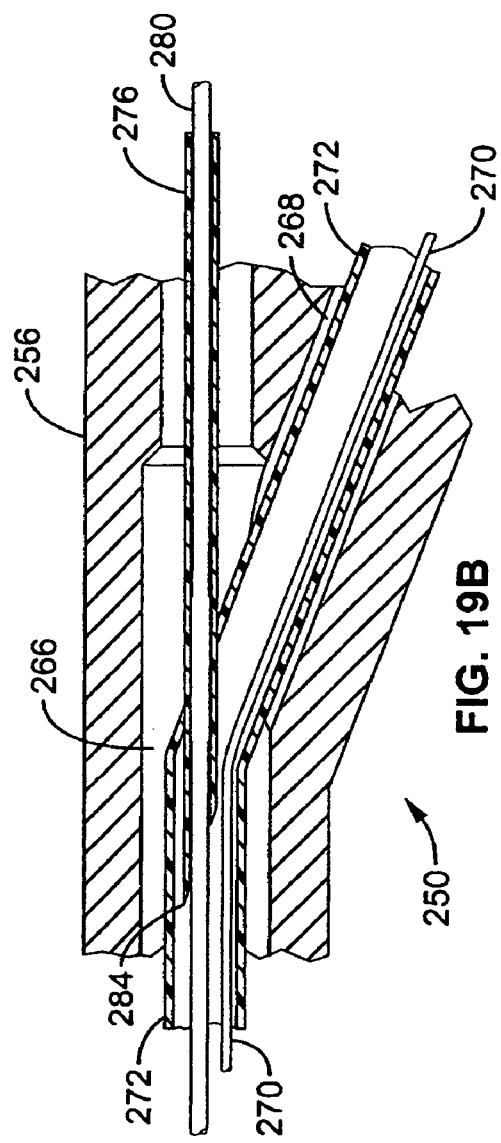

APPARATUS AND METHOD FOR INSERTING AN INTRA-AORTA CATHETER THROUGH A DELIVERY SHEATH

CROSS-REFERENCES TO RELATED APPLICATIONS

This application is a continuation of PCT Patent Application No. PCT/US03/29585 filed Sep. 22, 2003, which claims priority from U.S. Provisional Patent Application Ser. Nos.: 60/412,476, filed on Sep. 20, 2002; 60/486,206, filed on Jul. 9, 2003; and 60/502,399, filed on Sep. 13, 2003. The full disclosure of each of the foregoing applications is hereby incorporated by reference.

BACKGROUND OF THE INVENTION

1. Field of the Invention

This invention relates to the field of medical devices, and more particularly to a system and method for inserting a catheter for locally delivering fluids or agents within the body of a patient. Still more particularly, it relates to a system and method for inserting a catheter that locally delivers fluids or agents into branch blood vessels or body lumens from a main vessel or lumen, respectively, and in particular into renal arteries extending from an aorta in a patient.

2. Description of Related Art

Many different medical device systems and methods have been previously disclosed for locally delivering fluids or other agents into various body regions, including body lumens such as vessels, or other body spaces such as organs or heart chambers. Local "fluid" delivery systems may include drugs or other agents, or may even include locally delivering the body's own fluids, such as artificially enhanced blood transport (e.g. either entirely within the body such as directing or shunting blood from one place to another, or in extracorporeal modes such as via external blood pumps etc.). Local "agent" delivery systems are herein generally intended to relate to introduction of a foreign composition as an agent into the body, which may include a drug or other useful or active agent, and may be in a fluid form or other form such as gels, solids, powders, gases, etc. It is to be understood that reference to only one of the terms fluid, drug, or agent with respect to local delivery descriptions may be made variously in this disclosure for illustrative purposes, but is not generally intended to be exclusive or omissive of the others; they are to be considered interchangeable where appropriate according to one of ordinary skill in the art unless specifically described to be otherwise.

In general, local agent delivery systems and methods are often used for the benefit of achieving relatively high, localized concentrations of an agent that is injected within the body in order to maximize the intended effects locally while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed in locations throughout the body the body other than at the intended target.

Various diagnostic systems and procedures have been developed using local delivery of dye (e.g. radiopaque "contrast" agent) or other diagnostic agents, wherein an external monitoring system is able to gather important physiological information based upon the diagnostic agent's movement or assimilation in the body at the location of delivery and/or at other locations affected by the delivery site. Angiography is one such practice that uses a hollow, tubular angiography catheter for locally injecting radiopaque dye into a blood chamber or vessel, such as for example coronary arteries in the case of coronary angiography, or in a ventricle in the case of cardiac ventriculography.

Other systems and methods have been disclosed for locally delivering therapeutic agent into a particular body tissue within a patient via a body lumen. For example, angiographic catheters of the type just described above, and other similar tubular delivery catheters, have also been disclosed for use in locally injecting treatment agents through their delivery lumens into spaces within the body. More detailed examples of this type include local delivery of thrombolytic drugs such as TPA™, heparin, cumadin, or urokinase into areas of existing clot or thrombogenic implants or vascular injury. In addition, various balloon catheter systems have also been disclosed for local administration of therapeutic agents into target body lumens or spaces, and in particular associated with blood vessels. One example of this type of catheter include balloons with porous or perforated walls that elute drug agents through the balloon wall and into surrounding tissue such as blood vessel walls. Yet further examples for localized delivery of therapeutic agents include various multiple balloon catheters that have spaced balloons that are inflated to engage a lumen or vessel wall in order to isolate the intermediate catheter region from in-flow or out-flow across the balloons. According to these examples, a fluid agent delivery system is often coupled to this intermediate region in order to fill the region with agent such as drug that provides an intended effect at the isolated region between the balloons.

The diagnosis or treatment of many different types of medical conditions associated with various different body systems, organs, and tissues, may also benefit from the ability to locally deliver fluids or agents in a controlled manner. In particular, various conditions related to the renal system would benefit significantly from the capability of locally delivering therapeutic, prophylactic, or diagnostic agents into the renal arteries.

Acute renal failure ("ARF") is an abrupt decrease in the ability of the kidney to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or a-adrenergic agonists because of related systemic or renal vasoconstriction. Additionally, systemic vasodilation caused by anaphylaxis, and anti-hypertensive drugs, sepsis or drug overdose may also cause ARF because the body's natural defense is to shut down, i.e., the vasoconstriction of non-essential organs such as the kidneys. Reduced cardiac output caused by cardiogenic shock, congestive heart failure, pericardial tamponade or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve the administration of drugs. Examples of such drugs that have been used for this purpose include, without limitation: vasodilators, including for example papavarine, fenoldopam mesylate, calcium-channel blockers, atrial natriuretic peptide (ANP), acetylcholine, nifedipine, nitroglycerine, nitroprusside, adenosine, dopamine, and theophylline; antioxidants, such as for example acetylcysteine; and diuretics, such as for example mannitol, or furosemide. However, many of these drugs, when administered in systemic doses, have undesirable side effects. Additionally, many of these drugs would not be helpful in treating other causes of ARF. For example, while a septic shock patient with profound systemic vasodilation often has concomitant severe renal vasoconstriction, administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Surgical device interventions, such as hemodialysis, however, generally have not been observed to be highly efficacious for long-term management of CHF. Such interventions would also not be appropriate for many patients with strong hearts suffering from ARF.

The renal system in many patients may also suffer from a particular fragility, or otherwise general exposure, to potentially harmful effects of other medical device interventions. For example, the kidneys as one of the body's main blood filtering tools may suffer damage from exposure to high-density radiopaque contrast dye, such as during coronary, cardiac, or neuro angiography procedures. One particularly harmful condition known as "radiocontrast nephropathy" or "RCN" is often observed during such procedures, wherein an acute impairment of renal function follows exposure to such radiographic contrast materials, typically resulting in a rise in serum creatinine levels of more than 25% above baseline, or an absolute rise of 0.5 mg/dl within 48 hours. Therefore, in addition to CHF, renal damage associated with RCN is also a frequently observed cause of ARF. In addition, the function of the kidney is directly related to cardiac output and related blood pressure into the renal system. These physiological parameters, as in the case of CHF, may also be significantly compromised during a surgical intervention such as an angioplasty, coronary artery bypass, valve repair or replacement, or other cardiac interventional procedure. Therefore, the various drugs used to treat patients experiencing ARF associated with other conditions such as CHF have also been used to treat patients afflicted with ARF as a result of RCN. Such drugs would also provide substantial benefit for treating or preventing ARF associated with acutely compromised hemodynamics to the renal system, such as during surgical interventions.

There would be great advantage therefore from an ability to locally deliver such drugs into the renal arteries, in particular when delivered contemporaneously with surgical interventions, and in particular contemporaneously with radiocontrast dye delivery. However, many such procedures are conducted with medical device systems, such as using guiding catheters or angiography catheters having outer dimensions typically ranging between about 4 French to about 12 French, and ranging generally between about 6 French to about 8 French in the case of guide catheter systems for delivering angioplasty or stent devices into the coronary or neurovascular arteries (e.g. carotid arteries). These devices also are most typically delivered to their respective locations for use (e.g. coronary ostia) via a percutaneous, translumenal access in the femoral arteries and retrograde delivery upstream along the aorta past the region of the renal artery ostia. A Seldinger access technique to the femoral artery involves relatively controlled dilation of a puncture hole to minimize the size of the intruding window through the artery wall, and is a preferred method where the profiles of such delivery systems are sufficiently small. Otherwise, for larger systems a "cut-down" technique is used involving a larger, surgically made access window through the artery wall.

Accordingly, a system and method for inserting an intra-aorta catheter through a delivery sheath contemporaneous with other retrogradedly delivered medical device systems, such as of the types just described above, would preferably be adapted to allow for such interventional device systems, in particular of the types and dimensions just described, to pass upstream across the renal artery ostia (a) while the agent is being locally delivered into the renal arteries, and (b) while allowing blood to flow downstream across the renal artery ostia, and (c) in an overall cooperating system that allows for Seldinger femoral artery access. Each one of these features (a), (b), or (c), or any sub-combination thereof, would provide significant value to patient treatment; a local renal delivery system providing for the combination of all three features is particularly valuable.

Notwithstanding the clear needs for and benefits that would be gained from such a system and method for inserting an intra-aorta catheter through a delivery sheath, the ability to do so presents unique challenges.

Finally, among other additional considerations, previous disclosures have yet to describe an efficacious and safe system and method for positioning these types of local agent delivery devices at the renal arteries through a common introducer or guide sheath shared with additional medical devices used for upstream interventions, such as angiography or guide catheters. In particular, to do so concurrently with multiple delivery catheters for simultaneous infusion of multiple renal arteries would further require a guide sheath of such significant dimensions that the preferred Seldinger vascular access technique would likely not be available, instead requiring the less desirable "cut-down" technique.

Certain prior disclosures have provided surgical device assemblies and methods intended to enhance blood delivery into branch arteries extending from an aorta. For example, intra-aortic balloon pumps (IABPs) have been disclosed for use in diverting blood flow into certain branch arteries. One such technique involves placing an IABP in the abdominal aorta so that the balloon is situated slightly below (proximal to) the branch arteries. The balloon is selectively inflated and deflated in a counterpulsation mode (by reference to the physiologic pressure cycle) so that increased pressure distal to the balloon directs a greater portion of blood flow into principally the branch arteries in the region of their ostia. However, the flow to lower extremities downstream from such balloon system can be severely occluded during portions of this counterpulsing cycle. Moreover, such previously disclosed systems generally lack the ability to deliver drug or agent to the branch arteries while allowing continuous and substantial downstream perfusion sufficient to prevent unwanted ischemia.

Notwithstanding the interest and advances toward locally delivering agents for treatment or diagnosis of organs or tissues, the previously disclosed systems and methods summarized immediately above generally lack the ability to effectively deliver agents from within a main artery and locally into substantially only branch arteries extending therefrom while allowing the passage of substantial blood flow and/or other medical devices through the main artery past the branches. This is in particular the case with previously disclosed renal treatment and diagnostic devices and methods, which do not adequately provide for local delivery of agents into the renal system from a location within the aorta while allowing substantial blood flow continuously downstream past the renal ostia and/or while allowing distal medical device assemblies to be passed retrogradedly across the renal ostia for upstream use. Much benefit would be gained if agents, such as protective or therapeutic drugs or radiopaque contrast dye, could be delivered to one or both of the renal arteries in such a manner.

However, such previously disclosed designs would still benefit from further modifications and improvements in order to maximize the range of useful sizing for specific devices to accommodate a wide range of anatomic dimensions between patients; and optimize the construction, design, and inter-cooperation between system components for efficient, atraumatic use.

A need still exists for improved devices and methods for locally isolating delivery of fluids or agents into the renal arteries of a patient from a location within the patient's aorta adjacent the renal artery ostia along the aorta wall, and while allowing other treatment or diagnostic devices and systems, such as angiographic or guiding catheter devices and related systems, to be delivered across the location.

A need still exists for improved devices and methods for delivering both a local renal drug delivery system and at least one adjunctive distal interventional device, such as an angiographic or guiding catheter, through a common delivery sheath.

A need also still exists for improved devices and methods for delivering both a local renal drug delivery system and at least one adjunctive distal interventional device, such as an angiographic or guiding catheter, through a single access site, such as a single femoral arterial puncture.

A need still exists for an improved device configured with the necessary bore, transition angle and fittings to pass one or more devices smoothly into an introducer sheath lumen.

A need still exists for adjustable sheaths to allow placement of a local renal drug delivery system and aortic access with commercially available catheters and intervention equipment.

BRIEF SUMMARY OF THE INVENTION

One aspect of the invention is a method for providing a renal therapy system for use in a local renal therapy procedure in a patient by selecting an introducer sheath based on a length along a catheter that corresponds with a distance between a percutaneous vascular access site and a renal ostium. The introducer sheath is chosen from a plurality of introducer sheaths having different lengths.

One mode includes: accessing an abdominal aorta in the patient via the percutaneous access site; inserting the catheter through the percutaneous vascular access site; positioning a distal end of the catheter at a location within the abdominal aorta associated with a renal artery ostium; indicating the relative location of the percutaneous vascular access site on said catheter; and withdrawing said catheter and measuring the length from the percutaneous access point to the distal end of said catheter.

Another aspect of the invention is a local renal therapy system that includes an introducer sheath with a tubular wall with a tubular wall with a proximal end portion, a distal end portion that is adapted to be positioned at a location within an abdominal aorta associated with first and second renal ostia of first and second renal arteries, respectively, while the proximal end portion extends externally from the patient, and an introducer lumen that extends along a longitudinal axis between a proximal port along the proximal end portion and a distal port along the distal end portion. A bilateral renal delivery assembly with a local injection assembly that is adapted to be delivered to the location in a first condition through the introducer lumen is also provided. The introducer sheath has an adjustable length between a first configuration and a second configuration. In the first configuration the introducer sheath has a first length that is adapted to deliver the local injection assembly in a first condition to the location. In the second configuration the introducer sheath has a second length that is shorter than the first length and that corresponds with the local injection assembly extending in a second condition distally from the distal port at the location. In addition, in the second condition at the location the local injection assembly is adapted to be coupled to a source of fluid agent externally of the patient and to deliver a volume of fluid from the source bilaterally into each of the two renal arteries.

Another aspect of the invention is a system for locally delivering therapy to a renal system in a patient and that includes an introducer sheath in combination with a proximal coupler assembly as follows. The introducer sheath has an elongate tubular body with a proximal end portion, a distal end portion that is adapted to be placed percutaneously into a patient across a vascular access site when the proximal end portion extends externally from the patient, and a delivery lumen extending along a longitudinal axis between a proximal port along the proximal end portion and a distal port along the distal end portion. The proximal coupler assembly has a proximal portion and a distal portion. The distal portion comprises a distal lumen and is coupled to the proximal port with the distal lumen substantially aligned with the longitudinal axis of the delivery lumen. The proximal portion comprises a first branch lumen and a second branch lumen extending proximally from the distal lumen and terminating proximally at first and second entry ports, respectively. The first entry port is adapted to receive a percutaneous translumenal interventional device therethrough into the first branch lumen, whereas the second entry port is adapted to receive a bilateral renal delivery device assembly therethrough and into the second branch lumen. The first and second branch lumens are of sufficient orientation relative to the distal lumen, and the first and second branch lumens and distal and delivery lumens are of sufficient dimension, such that each of the percutaneous translumenal interventional device and the bilateral renal delivery device may be slideably engaged simultaneously within the distal lumen and further within the delivery lumen without substantial mutual interference therebetween.

Another aspect of the invention is a system for locally delivering therapy to a renal system in a patient that also includes an introducer sheath and a proximal coupler assembly as follows. The introducer sheath has an elongate tubular body with a proximal end portion, a distal end portion that is adapted to be placed percutaneously into a patient across a vascular access site when the proximal end portion extends externally from the patient, and a delivery lumen extending along a longitudinal axis between a proximal port along the proximal end portion and a distal port along the distal end portion. The proximal coupler assembly has a proximal portion and a distal portion. The distal portion comprises a distal lumen assembly and is coupled to the proximal port with the distal lumen assembly substantially aligned with the longitudinal axis of the delivery lumen. The proximal portion comprises a first branch lumen, a second branch lumen, and a third branch lumen coupled to and extending proximally from the distal lumen assembly and terminating proximally at first, second, and third entry ports, respectively. The first entry port is adapted to receive a percutaneous translumenal interventional device therethrough into the first branch lumen. The second entry port is adapted to receive a first delivery member of a bilateral renal delivery system therethrough and into the second branch lumen. The third entry port is adapted to receive a second delivery member of the bilateral renal delivery system therethrough and into the third branch lumen. Accordingly, the first, second, branch lumens are of sufficient orientation relative to the distal lumen assembly, and the first, second, and third branch lumens, distal lumen assembly, and delivery lumens are of sufficient dimension, such that each of the first and second delivery members of the bilateral renal delivery system and the percutaneous translumenal interventional device may be slideably engaged simultaneously within the distal lumen assembly and further within the delivery lumen without substantial mutual interference therebetween.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 2 illustrates a proximal coupler assembly in plan view according to the present invention.

FIG. 3 is a cross-sectional view of the proximal coupler assembly of FIG. 2 taken along the lines 3—3 of FIG. 4.

FIG. 5 illustrates a reduced volume proximal coupler assembly embodiment in plan view according to the present invention.

FIG. 6 illustrates the proximal coupler assembly of FIG. 5 in cross-sectional view taken along the lines 6—6 of FIG. 7.

FIG. 8 illustrates the proximal coupler assembly embodiment of FIG. 2 with an introducer sheath attached at the distal end.

FIG. 9 illustrates another embodiment of FIG. 8 where a side port is positioned between a secondary branch and an introducer sheath.

FIG. 16A illustrates another embodiment of an adjustable introducer sheath in an expanded state with an internal support tube positioned to prevent pleats from folding inward.

FIG. 16B illustrates the adjustable introducer sheath in FIG. 16A in a compressed state with the internal support tube removed.

FIG. 17A illustrates another embodiment of an adjustable introducer sheath with pleats, support wires and a locking ring.

FIG. 17B illustrates the adjustable introducer sheath shown in FIG. 17A with support wires retracted and the adjustable section compressed.

FIG. 19A, is a cut away cross-sectional view of FIG. 18 with the rigid tube advanced through the proximal port.

FIG. 19B is a cross-sectional view of the cut away view of FIG. 19A showing the pointed distal tip of rigid tube puncturing the delivery sheath.

DETAILED DESCRIPTION OF THE INVENTION

Figure 1:
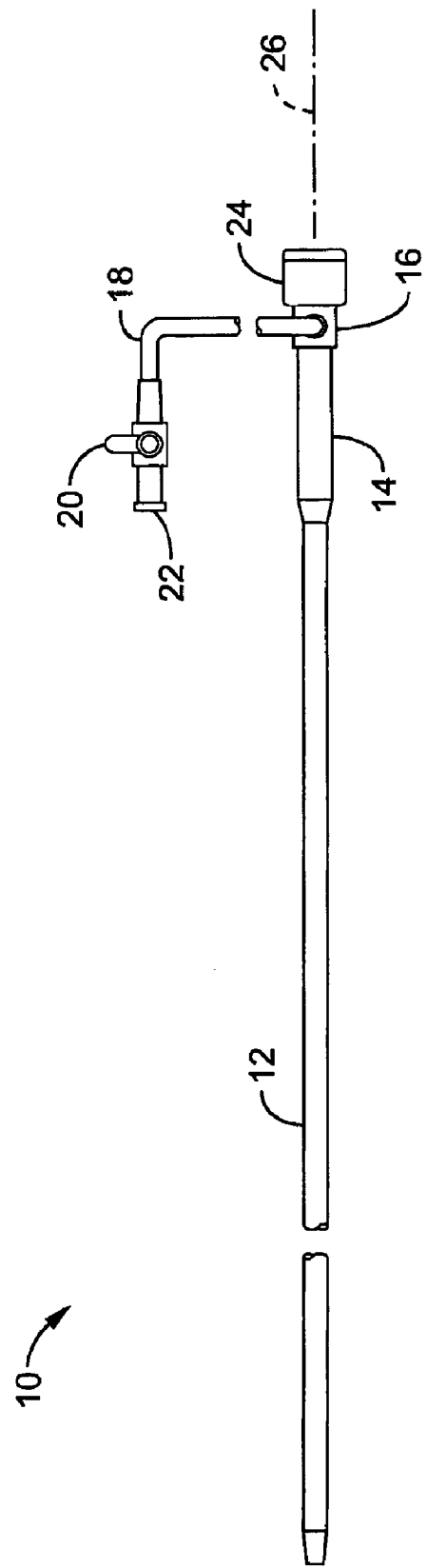
FIG. 1 illustrates a standard, single port catheter assembly as is known to exist in the art.

As will be appreciated by reference to the detailed description below and in further respect to the figures, the present invention is principally related to selective renal flow systems and methods, which are thus generally related to subject matter disclosed in the following prior filed co-pending U.S. Patent Applications that are commonly owned with the present application; Ser. No. 09/229,390 to Keren et al., filed Jan. 11, 1999 now U.S. Pat. No. 6,749,598, issued Jun. 15, 2004; Ser. No. 09/562,493 to Keren et al., filed May 1, 2000; and Ser. No. 09/724,691 to Kesten et al., filed Nov. 28, 2000, now allowed. The disclosures of these prior patent applications are herein incorporated in their entirety by reference thereto.

The invention is also generally related to certain aspects of subject matter disclosed in other Published International Patent Applications as follows: WO 00/41612 to Libra Medical Systems, published Jul. 20, 2000; and WO 01/83016 to Libra Medical Systems, published Nov. 8, 2001. The disclosures of these Published International Patent Applications are also herein incorporated in their entirety by reference thereto.

Various particular dimensions, constructions, and materials are herein described according to the various embodiments and are considered highly beneficial. However, it is contemplated that such are illustrative and other modifications may be made to suit a particular need without departing from the intended present scope.

Referring more specifically to the drawings, for illustrative purposes the present invention is embodied in the apparatus generally shown in FIG. 1 through FIG. 22. It will be appreciated that the apparatus may vary as to configuration and as to details of the parts, and that the method may vary as to the specific steps and sequence, without departing from the basic concepts as disclosed herein.

The description herein provided relates to medical material delivery systems and methods in the context of their relationship in use within a patient's anatomy. Accordingly, for the purpose of providing a clear understanding, the term proximal should be understood to mean locations on a system or device relatively closer to the operator during use, and the term distal should be understood to mean locations relatively further away from the operator during use of a system or device. The present embodiments described below generally relate to the local delivery of renal drugs from within the renal arteries themselves; however, it is contemplated that these systems and methods may be suitably modified for use in other anatomical regions and for other medical conditions without departing from the broad scope of various of the aspects illustrated by the embodiments.

In general, the disclosed material delivery systems will include a fluid delivery assembly, a proximal coupler assembly and one or more elongated bodies, such as tubes or catheters. These elongated bodies may contain one or more delivery lumens and generally consist of a proximal region, a mid-distal region, and a distal tip region or regions in the case of multi-tipped embodiments. The distal tip region will typically have means for delivering a material such as a fluid agent. Radiopaque markers or other devices may be coupled to the specific regions of the elongated body to assist introduction and positioning.

The material delivery system of the present invention is intended to be placed into position by a physician, typically either an interventionalist (cardiologist or radiologist) or an intensivist, a physician who specializes in the treatment of intensive-care patients. The physician will gain access to a femoral artery in the patient's groin, typically using a Seldinger technique of percutaneous vessel access or other conventional method.

FIG. 1 illustrates a standard, single port catheter assembly 10 as is known to exist in the art with introducer sheath 12 coupled to tubular hub 14. Side port 16 is in fluid communication with hub 14 and introducer sheath 12 and has tube 18 connected to valve 20 and fitting 22 for introduction of saline or other fluids into catheter assembly 10. Hemostasis valve 24 is coupled to hub 14 and positioned on the axis 26 of introducer sheath 12 and allows sealable introduction of guide wires, catheters and other interventional devices (not shown) into hub 14.

Figure 4:
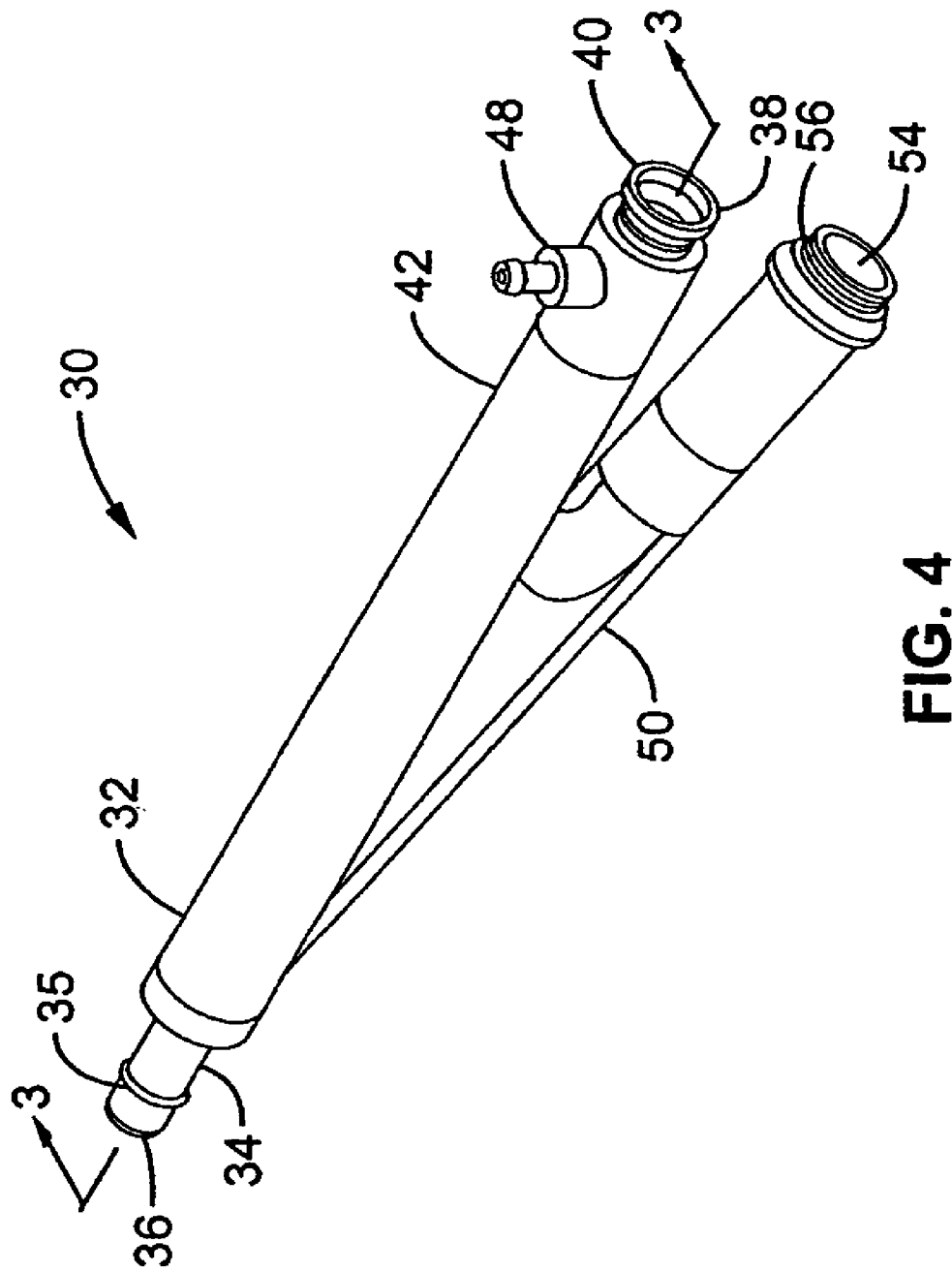
FIG. 4 illustrates the proximal coupler assembly of FIG. 2 in perspective view.

FIG. 2 through FIG. 4 illustrate an embodiment of the present invention, a proximal coupler assembly 30, in plan view, sectional view and perspective view respectively. In the embodiment shown, the Y hub body 32 is configured with an introducer sheath fitting 34 that has outer rib 35 at the distal end 36 of Y hub body 32 and a main adapter fitting 38 at the proximal end 40 of hub body 32. In an exemplary embodiment, main adapter fitting 38 mates with a hemostasis valve (shown in FIG. 8). Main branch 42 has tubular main channel 44 aligned on axis 46 and fluidly connects introducer sheath fitting 34 and main hemostasis adapter fitting 38, also aligned on axis 46. By way of example and not of limitation, main channel 44 may accommodate a 6 Fr Guide catheter (not shown). Side port fitting 48 is positioned on main branch 42 and is fluidly connected to main channel 44. Secondary branch 50 has tubular branch channel 52 that intersects main channel 44 at predetermined transition angle β. Proximal end 54 of secondary branch 50 has secondary fitting 56. In a beneficial embodiment, secondary fitting 56 is adapted to mate with a Touhy Borst valve (shown in FIG. 8). In the present embodiment, a channel restriction 58 is molded into introducer sheath fitting 34. The Y hub body 32 may be molded in one piece or assembled from a plurality of pieces. In one embodiment, (not shown) side port fitting 48 is placed on secondary branch 50 in similar fashion as that shown on main branch 42 in FIG. 1–FIG. 3.

Figure 7:
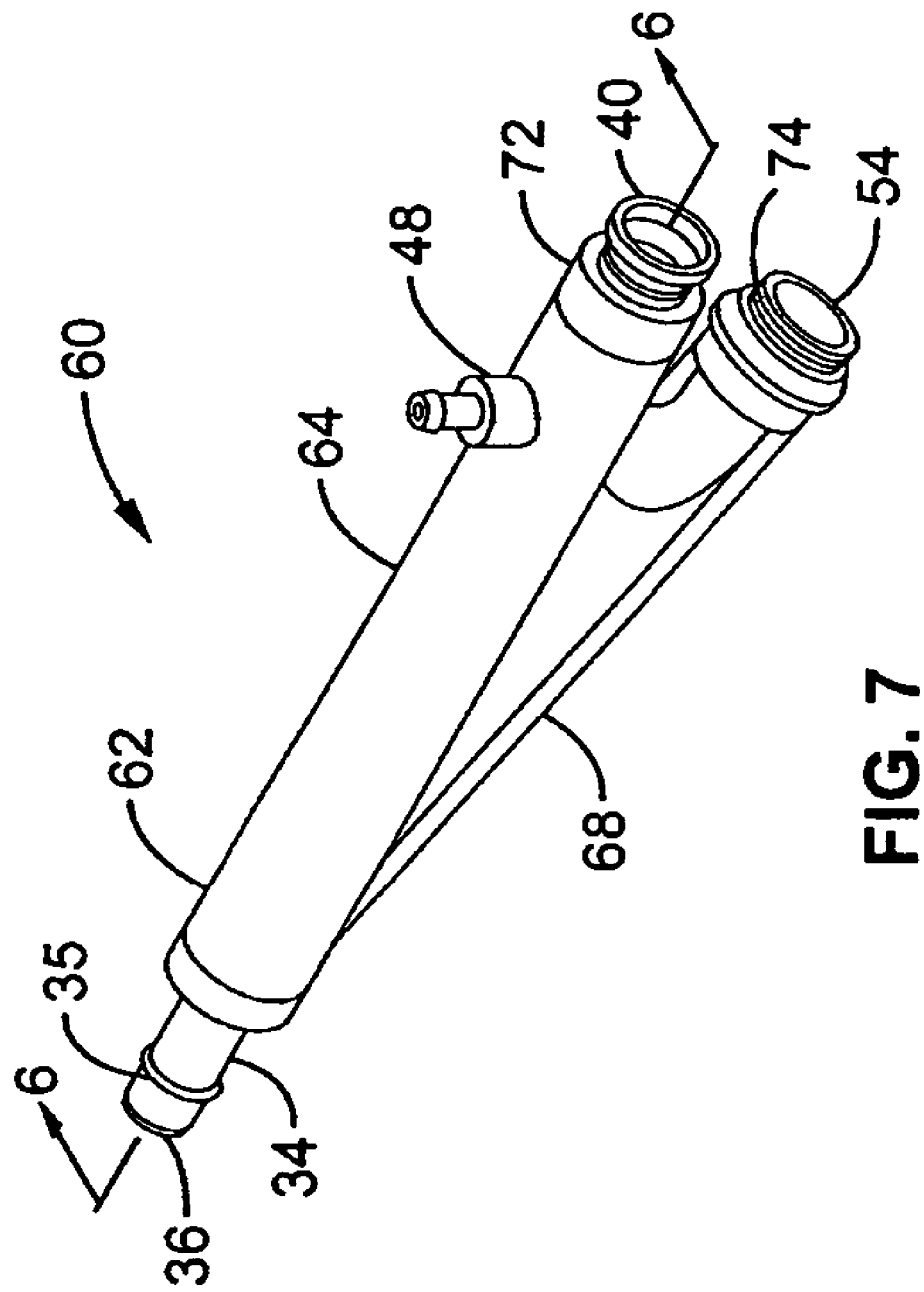
FIG. 7 illustrates the proximal coupler assembly of FIG. 5 in perspective view.

Turning now to FIG. 5 through FIG. 7, another beneficial embodiment of a reduced volume proximal coupler assembly 60, in plan view, section view, and perspective view respectively are shown. The Y hub body 62 is adapted with a reduced size main branch 64 and a reduced volume main channel 66. Secondary branch 68 and secondary channel 70 also present a reduced volume. Introducer sheath fitting 34 at the distal end 36 and side port fitting 48 are the same as in FIG. 2 through FIG. 5. Hemostasis adapter fitting 72 at distal end 40 of main branch 64 is adapted for reduced volume operation. Secondary fitting 74 at proximal end 54 of secondary branch 68 is also adapted for reduced volume operation.

FIG. 8 illustrates the proximal coupler assembly 30 as described in FIG. 2 through FIG. 4 with proximal end 75 of introducer sheath 76 coupled to introducer sheath fitting 34 of Y hub body 32. Introducer sheath fits over introducer sheath fitting 34 and is secured by rib 35 (shown in FIG. 2 through FIG. 7). Distal end 77 of introducer sheath 76 may be adapted with a truncated conical shape to aid insertion and advancement of introducer sheath 76. In one mode, distal end 77 of introducer sheath is further adapted to accommodate a vessel dilator. In another mode, distal end 77 of introducer sheath is further adapted with a radiopaque marker (not shown). By way of example and not of limitation, introducer sheath may be sized up to about 10 Fr and may be about 8 Fr. In a beneficial embodiment, introducer sheath is about 30 cm in length to about 45 cm in length. Fluid fitting 78 and a fluid valve 80, such as a stopcock valve, are connected to side port 48 with fluid tube 82. In one mode, saline solution is introduced into fluid fitting 78 through fluid valve 80 and into Y hub assembly 32. A hemostasis valve 84 is coupled to main adapter fitting 38. A Touhy Borst valve 86 is coupled to secondary fitting 56. It is to be appreciated that proximal coupler assembly 30 with hemostasis valve 84, Touhy Borst valve 86 and introducer sheath 76 attached, may be configured as a kit. It is also to be appreciated that Touhy Borst valve 86 could be placed in addition or instead on main branch of hub body 32 and likewise hemostasis valve 84 could also be placed in addition or instead on side branch 50. Similarly, it can be appreciated by one skilled in the art that side port 48 and associated fluid tube 82, fluid valve 80, and fluid fitting 78 could be placed in addition or instead on side branch 50 of Y hub body 32.

FIG. 9 illustrates another embodiment of a proximal coupler as shown in FIG. 8 where the proximal coupler assembly 90 has side port 48 positioned on Y hub assembly 92 between secondary branch 94 and an introducer sheath fitting 96. Introducer sheath 76 with proximal end 75 and distal end 77 is shown coupled to Y hub assembly 92 at introducer sheath fitting 96.

Figure 10:
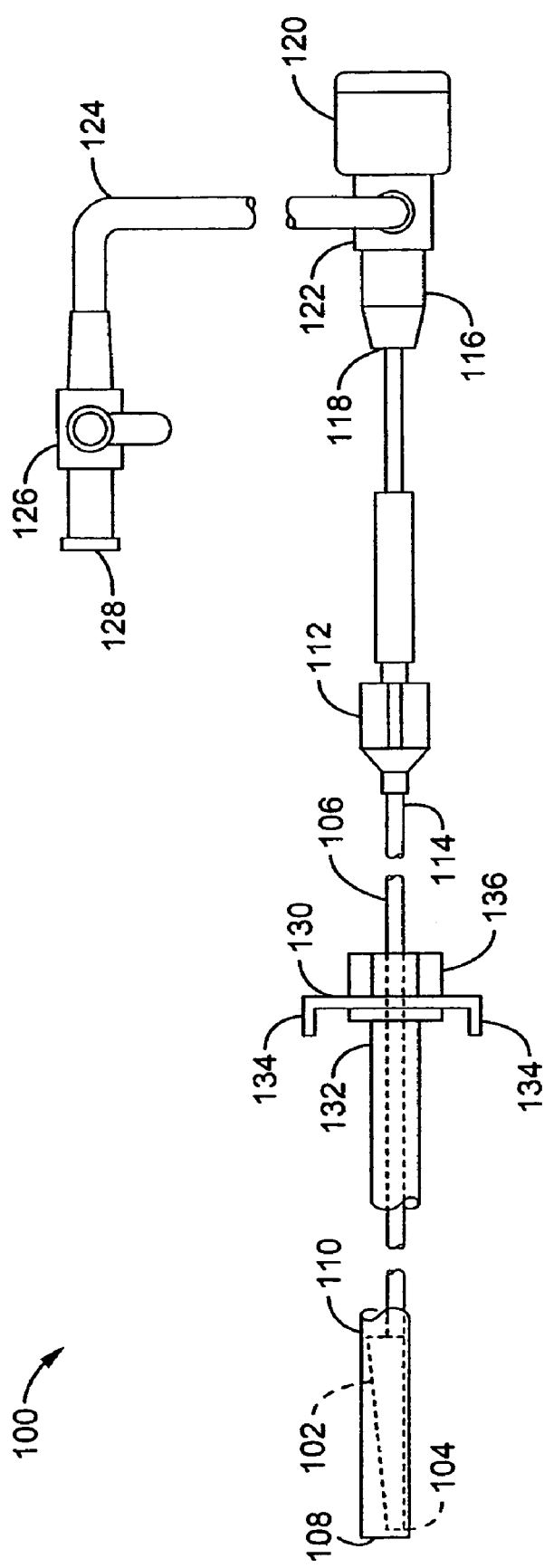
FIG. 10 illustrates a local fluid delivery system according to one embodiment of the invention.

FIG. 10 illustrates a fluid delivery system 100 before insertion. A fluid agent infusion device 102, shown in phantom, is positioned on the distal end 104 of a stiff tube 106 and compressed in the distal end 108 of delivery sheath 110. By example and not by limitation, delivery sheath 110 may be about 6 Fr to about 8 Fr in diameter and about 15 cm in length. In another embodiment, stiff tube 106 is made of a Nickel-Titanium alloy. A torque handle 112 is coupled to stiff tube 106 at a mid proximal position 114 on stiff tube 106. A fluid infusion port 116 is positioned at the proximal end 118 of stiff tube 106. Fluid infusion port 116 is coupled to an adapter 120 for fluid infusion. Side port fitting 122 is coupled to tube 124 and further coupled to fluid valve 126 and fluid fitting 128. In an exemplary embodiment, fluid infusion port 116 is adapted for a Luer fitting. In another exemplary embodiment, side port fitting 122 is used for injecting a saline solution.

Delivery sheath handle 130 is positioned and attached firmly at the proximal end 132 of delivery sheath 110. Delivery sheath handle 130 is further comprised of delivery handle tabs 134 and delivery handle cap 136. In an exemplary embodiment, delivery sheath handle 130 is configured to break symmetrically in two parts when delivery handle cap 136 is removed and delivery handle tabs 134 are forced apart. By way of example and not of limitation, distal end 104 of stiff tube 106 can be configured to couple to bifurcated catheters, flow diverters, and other devices configured to infuse fluids into a major blood vessel or one or more branch blood vessels. By way of example and not of limitation distal end 104 of stiff tube 106 can be configured with radiopaque markers or other diagnostic devices to aid in positioning.

Figure 11A:
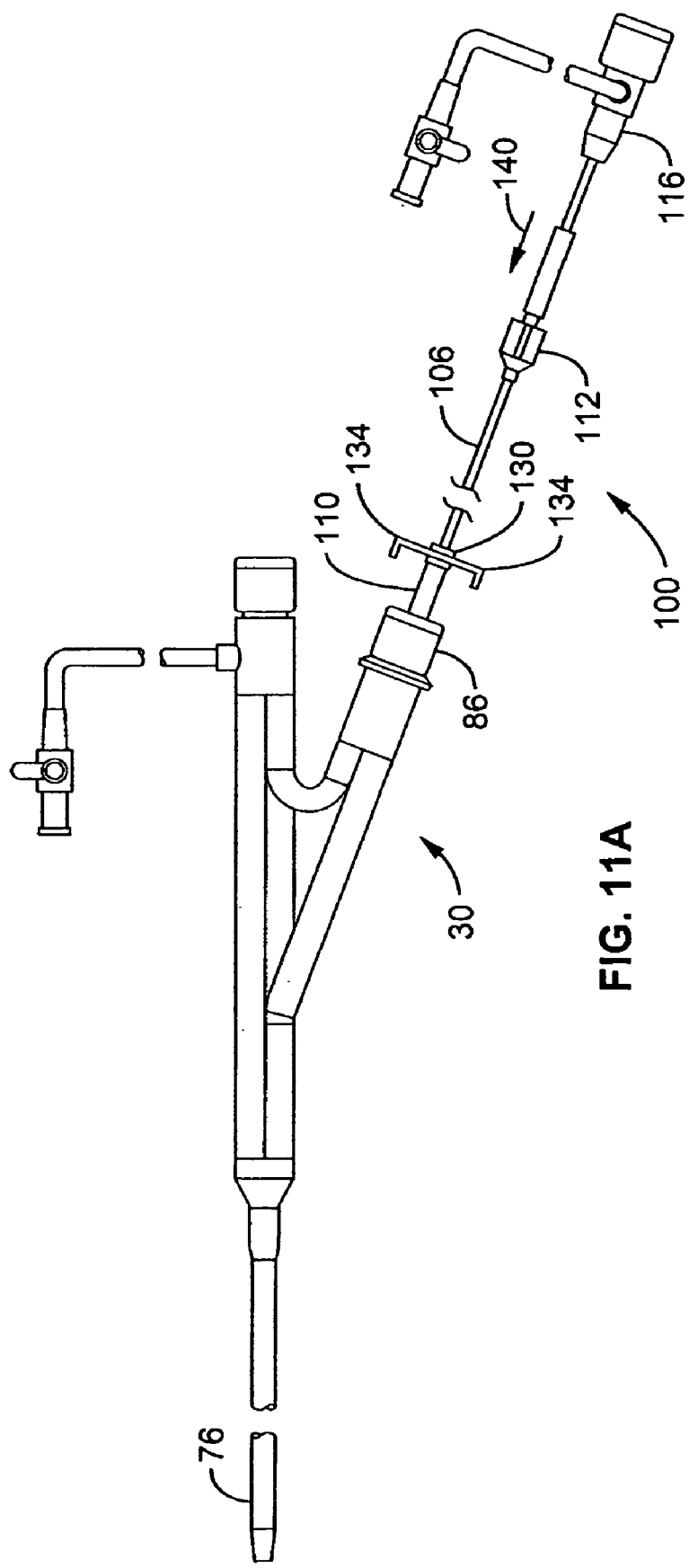
FIG. 11A illustrates a local fluid delivery system as shown in FIG. 10 in the branch port of a proximal coupler assembly.
Figure 11B:
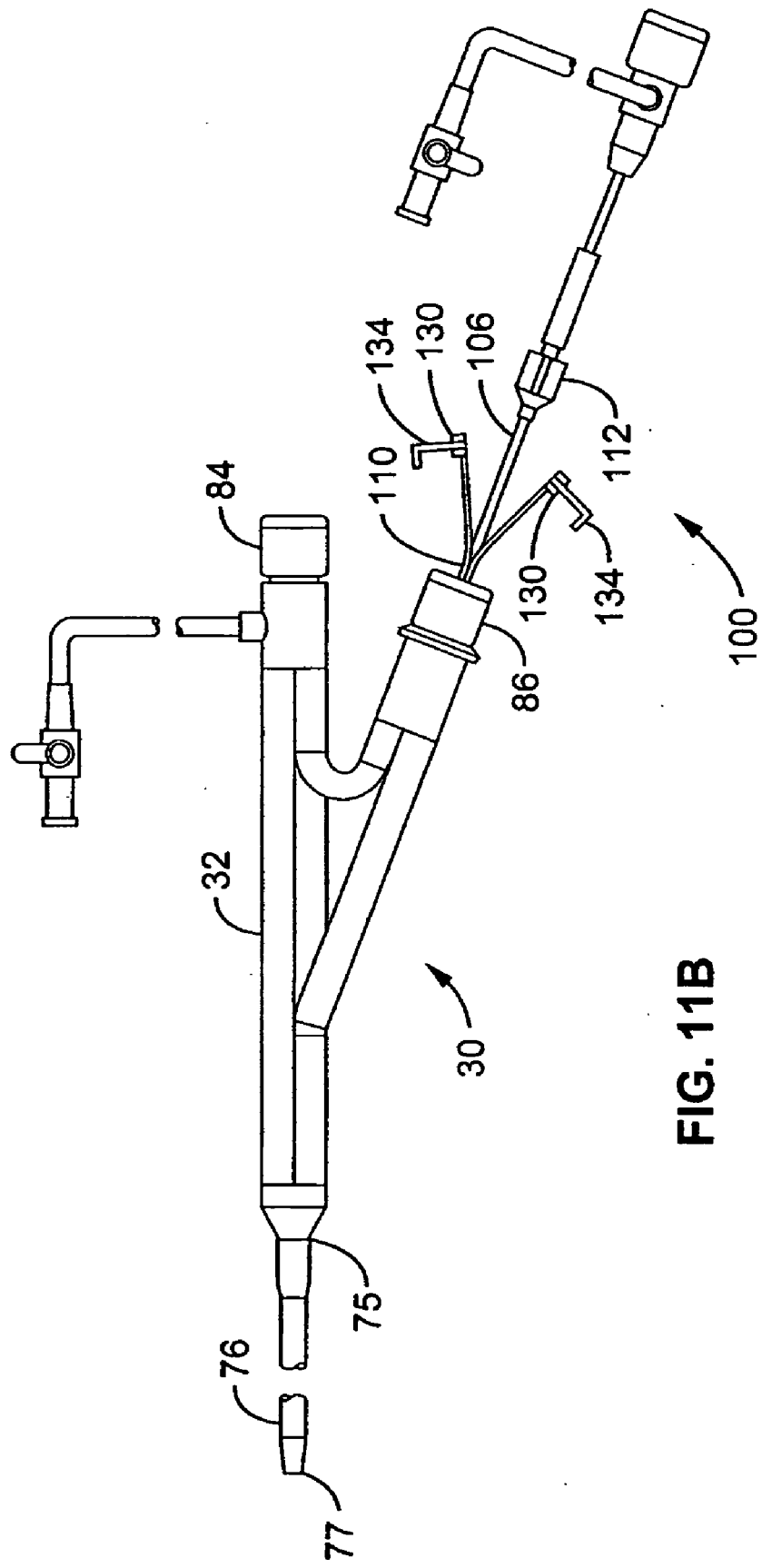
FIG. 11B illustrates a local fluid delivery system as shown in FIG. 11A with the stiff tube advanced and the tear away sheath separated.

FIG. 11A and FIG. 11B illustrate a fluid delivery system 100 as shown in FIG. 10, inserted into a Y hub assembly 30 as previously shown in FIG. 8. Details of Y hub assembly are omitted for clarity. In FIG. 11A, delivery sheath 110 is inserted through Touhy Borst valve 86 through secondary branch channel 52 (see FIG. 3) until distal end 108 of delivery catheter 110 (see FIG. 10) stops against channel restriction 58 (see FIG. 3). Force 140 is applied in a distal direction at torque handle 112 to push stiff tube 106 through delivery tube 110. Fluid agent infusion device 102 (see FIG. 10) travels distally into introduction sheath 76.

In FIG. 11B, stiff tube 106 has been advanced through introduction sheath 76 and fluid agent infusion device 102 shown in FIG. 10 is deployed into introduction sheath 76. In one embodiment, distal end 77 of introducer sheath 76 is positioned above the renal arteries (shown in FIG. 12) prior to deploying fluid agent infusion device 102 shown in FIG. 10. In another embodiment, distal end 77 of introducer sheath 76 is retracted in a proximal direction while fluid agent infusion device 102 shown in FIG. 10 remains positioned proximal the renal arteries. Delivery sheath 110 is retracted from main channel 44 (see FIG. 3) of Y hub assembly 32 to allow a medical intervention device (see FIG. 12) to enter hemostasis valve 84 for further advancement through main channel 44 (see FIG. 3), through introducer sheath 76 and along side stiff tube 106. In one mode, delivery sheath 110 is removed from Y hub assembly 32 after positioning fluid agent device 102 in introducer sheath 76. In one exemplary embodiment, delivery sheath 110 is extruded with two thin wall positions about 180 degrees apart on its circumference to facilitate splitting. In one mode, delivery sheath handle 130 is split in two by removing delivery handle cap 136 (see FIG. 10) and pressing inwardly on delivery handle tabs 134. Delivery sheath may be split by pulling delivery tabs 134 apart. By way of example and not of limitation, delivery sheath 110 may be completely removed through Touhy Borst valve 86 before splitting and removing by tearing away. It is to be appreciated that proximal coupler assembly 30 with introducer sheath 76 and fluid delivery system 100 together may be configured as a kit.

Figure 12:
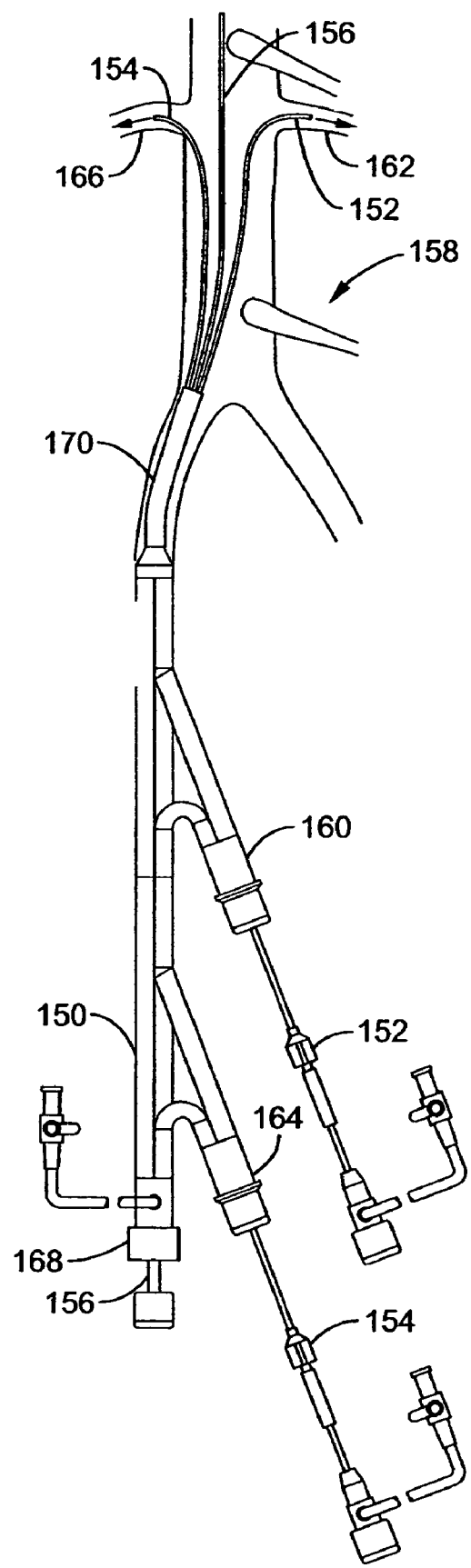
FIG. 12 is a stylized illustration of a double Y assembly with two local fluid delivery systems and an intervention catheter disposed in an aorta system of a patient according to the present invention.

FIG. 12 is a stylized illustration of a double Y proximal coupler 150 with two local fluid delivery systems 152, 154 and an intervention catheter 156 in an aorta system 158. Details of local fluid delivery systems 152, 154 are shown in FIGS. 11A and 11B and are omitted here for clarity. The double Y proximal coupler 150 is constructed similar to a proximal coupler assembly 30 as shown in FIG. 2 through FIG. 4 but with another branch port added. Secondary branch 160 accommodates local fluid delivery system 152 for drug infusion in right renal artery 162. Tertiary branch 164 accommodates local fluid delivery system 154 for drug infusion in left renal artery 166. Interventional catheter 156 enters double Y proximal coupler 150 through hemostasis valve 168. Introduction sheath 170 is sized to accommodate local fluid delivery systems 152, 154 and catheter 156 simultaneously. FIG. 12 illustrates secondary branch 160 and tertiary branch 164 on the same side of the double proximal coupler; however, they may be positioned on opposite sides or in another beneficial configuration. By way of example and not of limitation, the cross section of local fluid delivery system 152, 154 may be oval shaped. By way of example and not of limitation, double Y proximal coupler 150 may be adapted to advance a wide mix of medical devices such as guide wires, diagnostic catheters, flow diverters and infusion assemblies through introducer sheath 170 and into a vascular system such as aorta system 158.

Figure 13A:
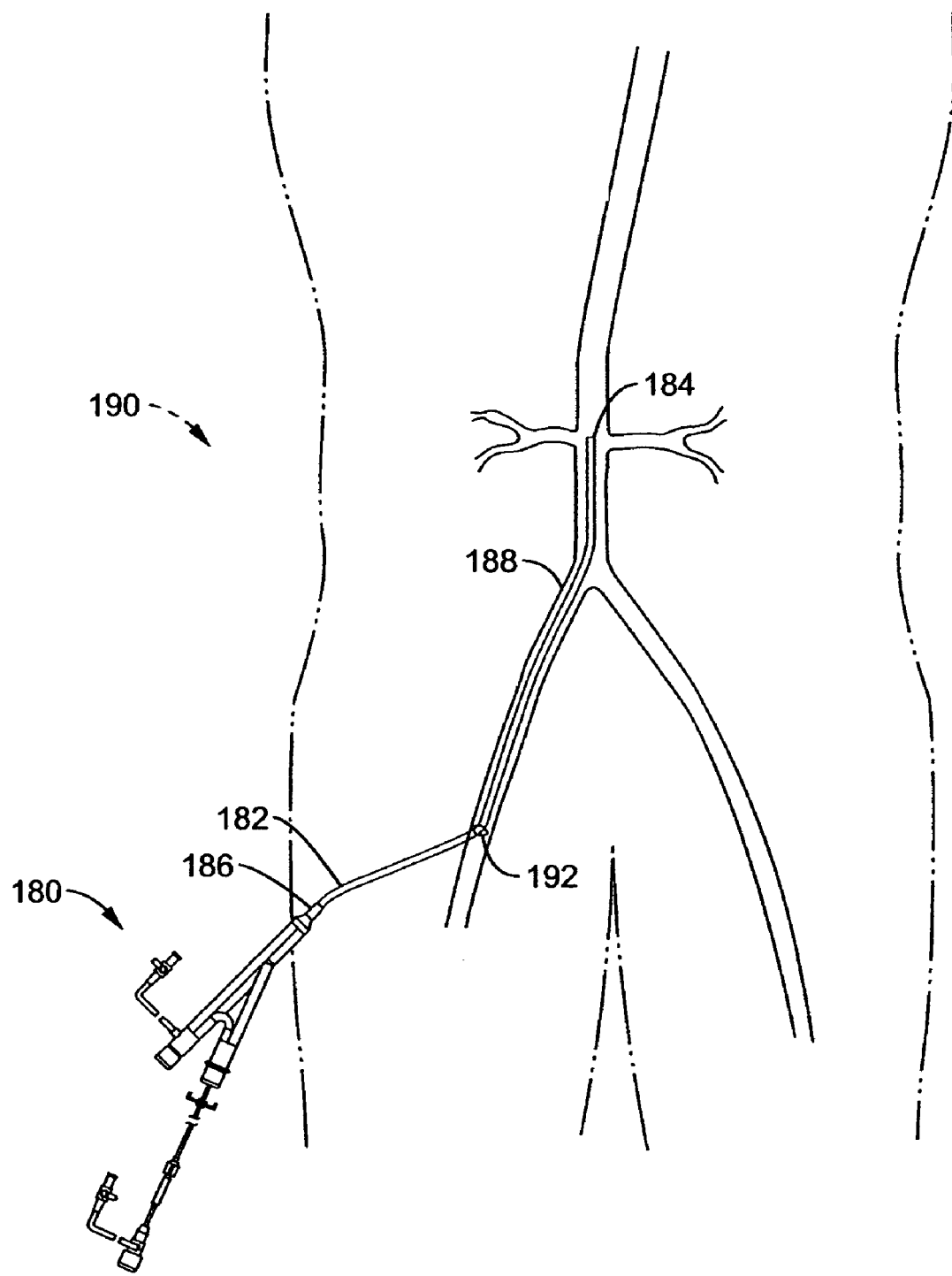
FIG. 13A illustrates a proximal coupler assembly similar to that shown in FIG. 11A with an introducer sheath inserted in an aorta system of a patient.

FIG. 13A illustrates a proximal coupler with a fluid delivery system attached, designated as coupler assembly 180, similar to that shown in FIG. 11 A. Coupler assembly 180 is coupled to introducer sheath 182 with a distal end 184 and a proximal end 186, inserted in aorta system 188 of patient 190 via femoral or iliac arterial access point 192. Details of proximal coupler assembly 180, as previously described in FIG. 11A and FIG. 11B, have been omitted for clarity.

Figure 13B:
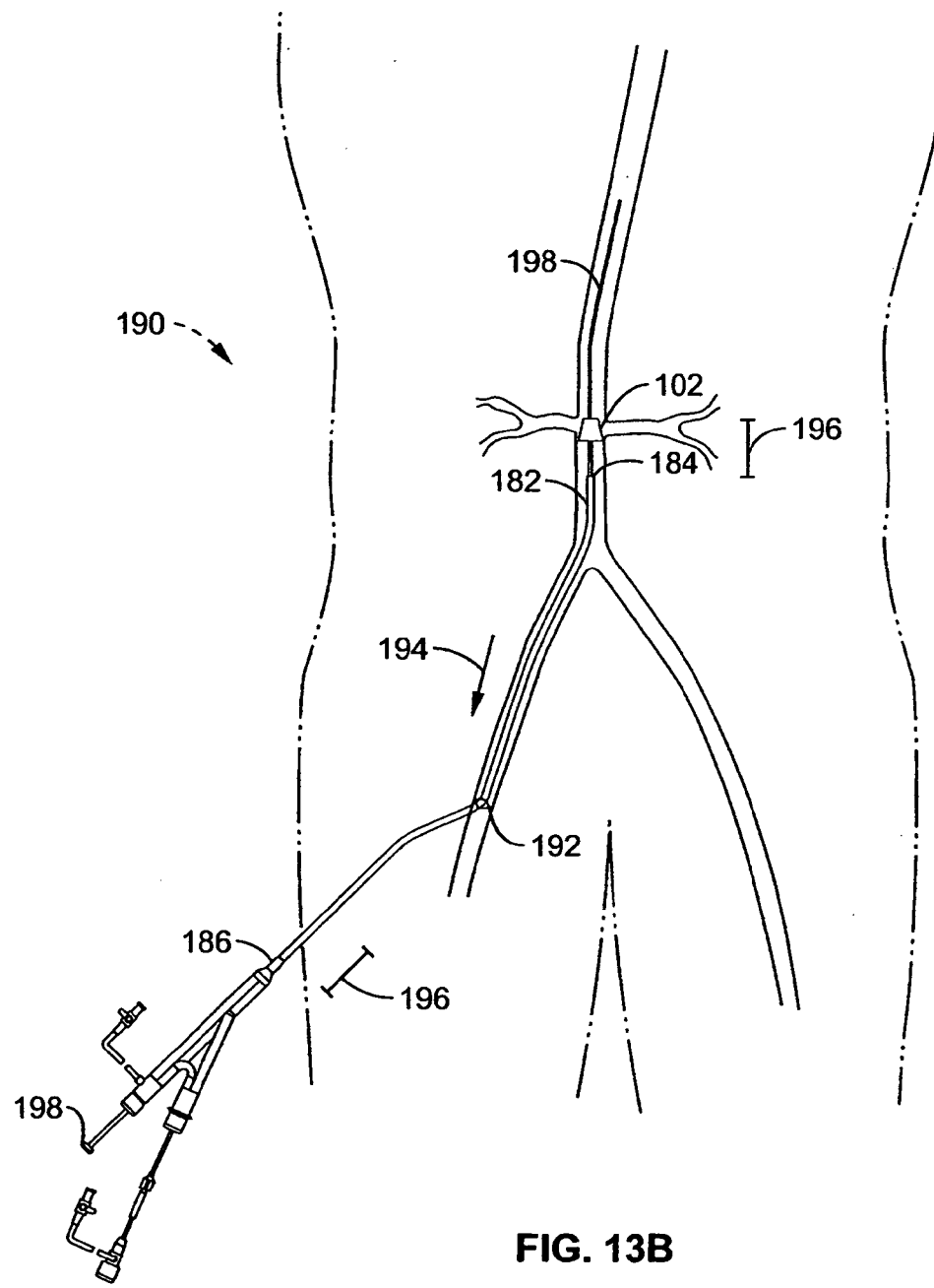
FIG. 13B is an illustration of the introducer sheath shown in FIG. 13A retracted and pulled away from the insertion point.

In FIG. 13B, introducer sheath 182 has been retracted in direction 194 to deploy a fluid agent infusion device 102 (as shown in FIG. 10) and create transition zone 196. As a result, proximal end 186 of introducer sheath 182 is pulled away from and outside of insertion point 192 by a length corresponding to the length of transition zone 196. Interventional catheter 198 must be extended the length of transition zone 196 to reach a target medical location (not shown) distal of fluid agent infusion device 102, when introducer sheath 182 is in a retracted position.

Figure 14A:
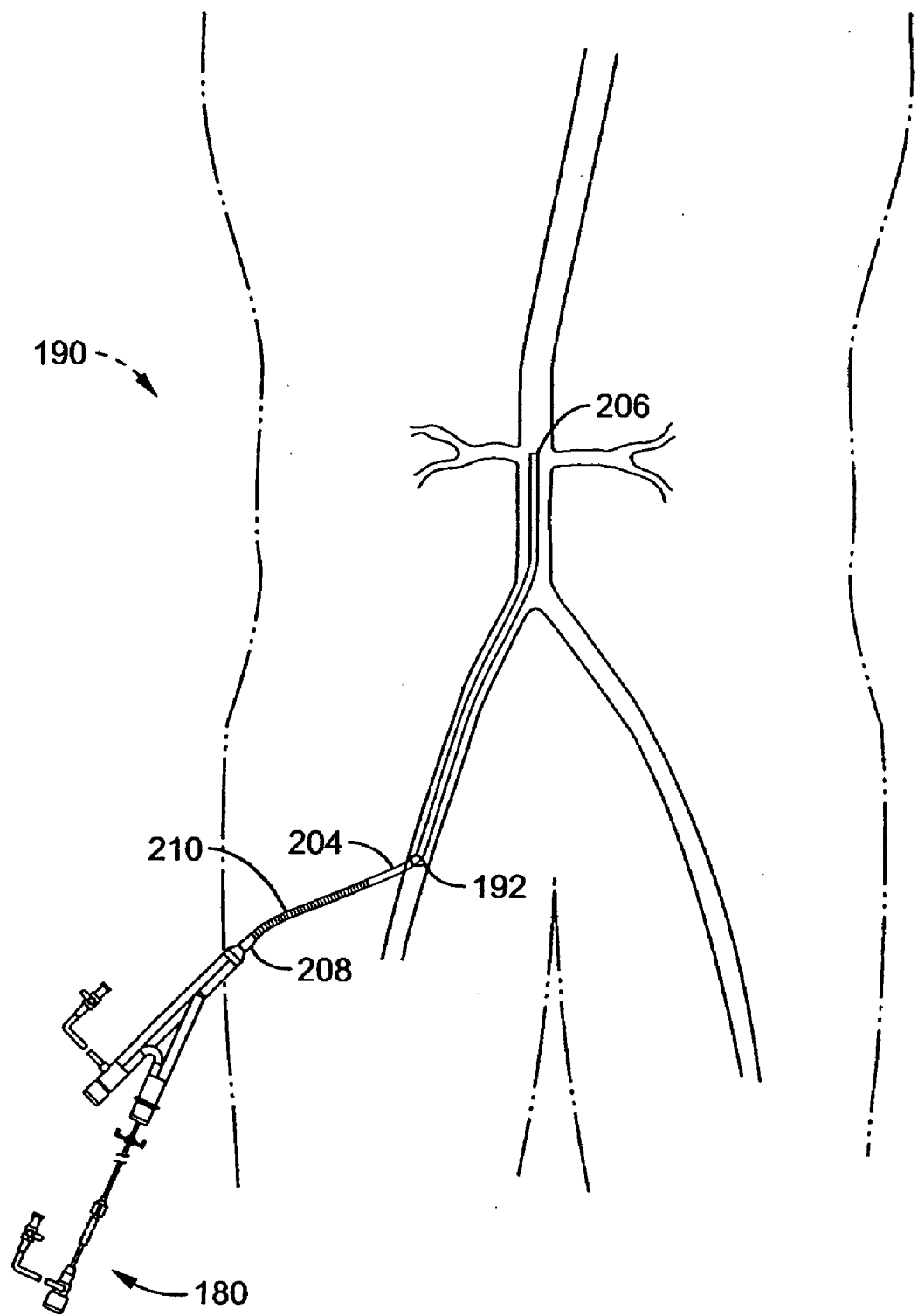
FIG. 14A illustrates an adjustable introducer sheath in an expanded state.

FIG. 14A illustrates the proximal coupler fluid delivery assembly 180 of FIG. 13A with adjustable introducer sheath 204 having a distal end 206, a proximal end 208 and an adjustable proximal section 210 in an expanded state. Adjustable proximal section 210 of adjustable introducer sheath 204 is composed of a corrugated flexible material to allow compression in total length in "accordion" fashion.

Figure 14B:
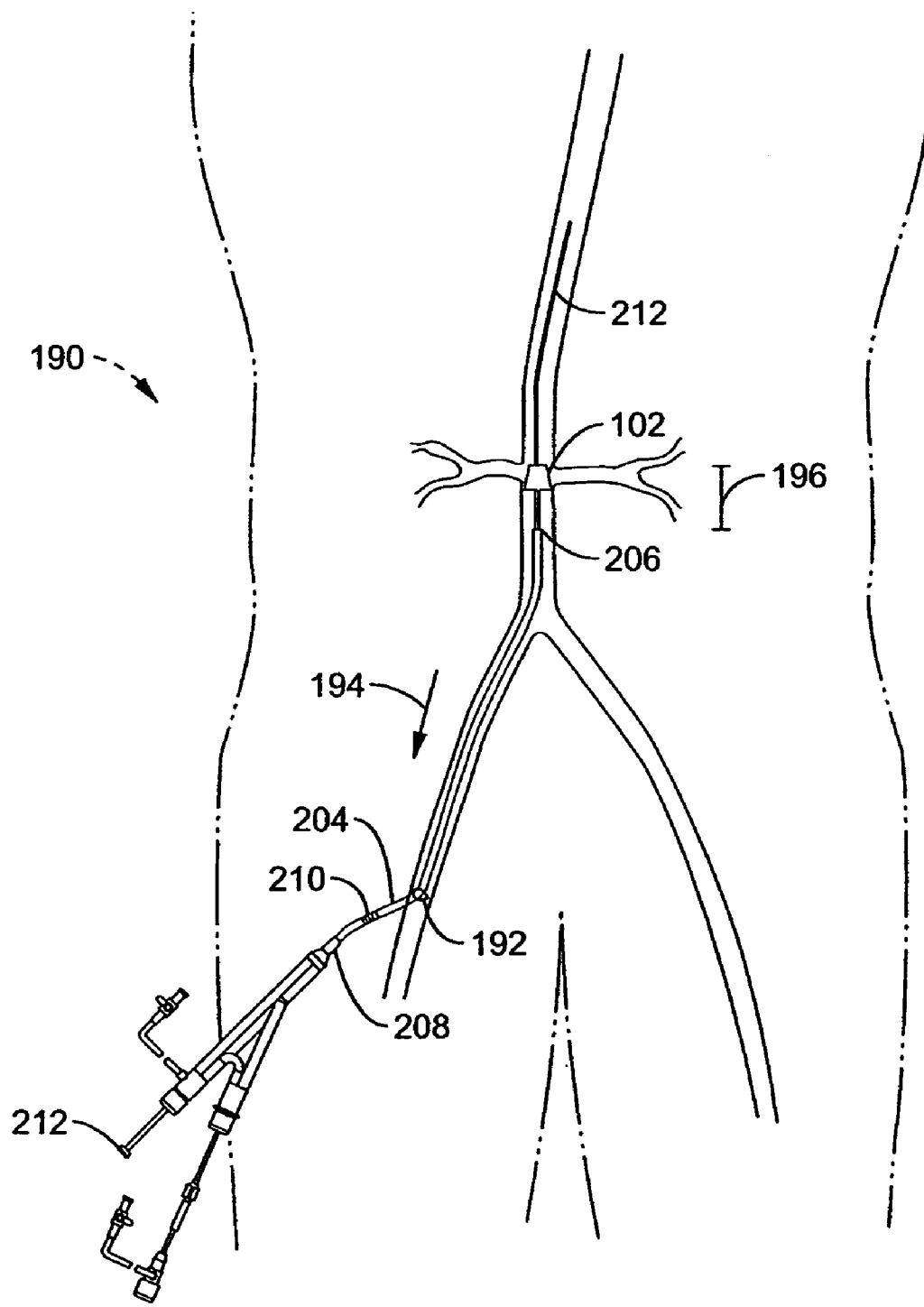
FIG. 14B illustrates the adjustable introducer sheath shown in FIG. 14A in a compressed state.

FIG. 14B illustrates adjustable introducer sheath 204, shown in FIG. 14A with adjustable proximal section 210 in a compressed state, such as after deploying a fluid agent infusion device 102 where retraction of distal end 206 of introducer sheath 204 in direction 194 creates transition zone 196. Proximal end 208 of adjustable introducer sheath 204 is not pulled away from insertion point 192 because of compression of adjustable proximal section 210 by the length of transition zone 196. Interventional catheter 212 is of adequate length and reaches target medical location (not shown) upstream of fluid agent infusion device 102.

Figure 15A:
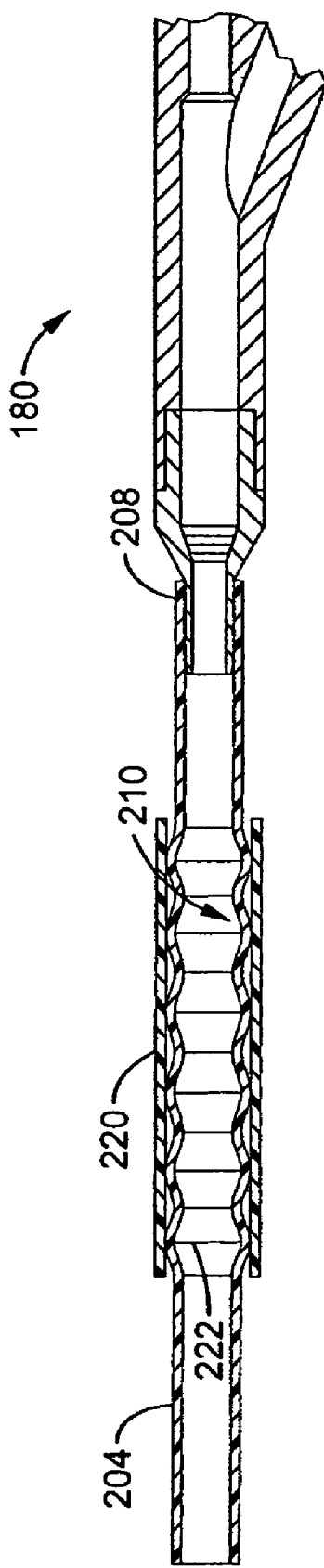
FIG. 15A illustrates an adjustable introducer sheath with an external retaining tube positioned over the pleats.

FIG. 15A illustrates a close up of a proximal coupler assembly 180 with an adjustable introducer sheath 204 coupled at proximal end 208 with adjustable proximal section 210 in an expanded state as shown in FIG. 14A. A low profile, external retaining tube 220 is positioned snugly over the pleats 222 of adjustable proximal section 210 and prevents pleats 222 from folding outward and thus, prevents adjustable proximal section 210 from contracting.

Figure 15B:
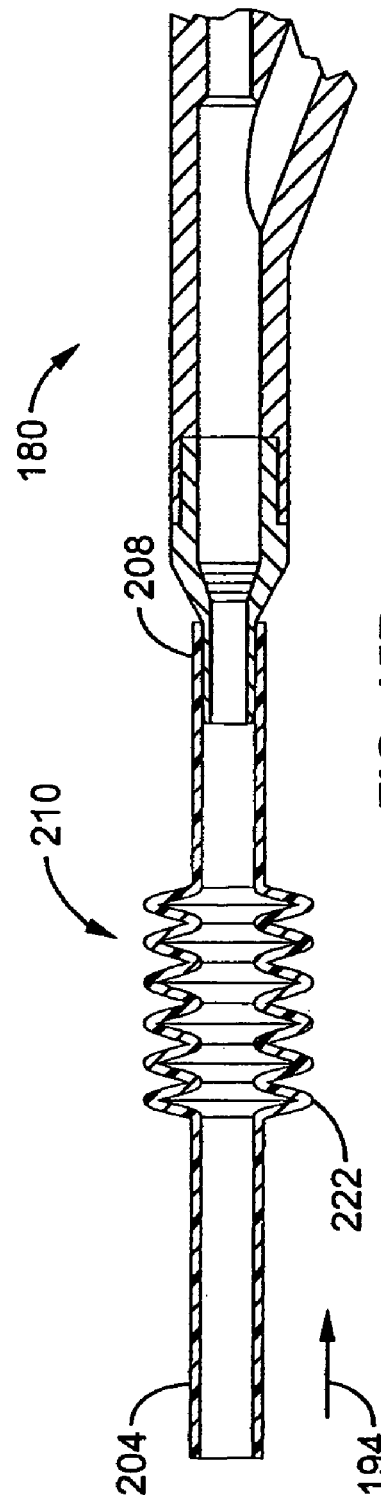
FIG. 15B illustrates the adjustable introducer sheath in FIG. 15A with the external retaining tube removed from the pleats.

FIG. 15B illustrates the adjustable introducer sheath 204 shown in FIG. 15A with external retaining tube 220 removed from adjustable proximal section 210. Pleats 222 can fold outward allowing adjustable section 210 to contract in direction 194. By way of example and not of limitation, external retaining tube 220 can slide to another section of introducer sheath 204 or can be removed in a tear-away fashion.

FIG. 16A illustrates another embodiment of a proximal coupler assembly 180 coupled to an adjustable introducer sheath 204 at proximal end 208 with adjustable proximal section 210 in an expanded state as shown in FIG. 14A. Internal support tube 224 is positioned in adjustable proximal section 210 such that the outer diameter of internal support tube 224 prevents pleats 222 from folding inward.

FIG. 16B illustrates the adjustable introducer sheath 204 in FIG. 16A with internal support tube 224 removed from adjustable proximal section 210. Pleats 222 fold inward allowing adjustable section 210 to contract. Internal support tube 224 can alternatively be positioned in another section of introducer sheath 204 through external manipulation of adjustable proximal section 210 (not shown).

FIG. 17A illustrates another embodiment of a proximal coupler assembly 180 coupled to proximal end 208 of adjustable introducer sheath 204. Adjustable section 210 of introducer sheath 204 has pleats 222, distal end 226 and proximal end 228. A plurality of adjusting wires 230 are coupled to introducer sheath 204 at distal end 226 of adjustable section 210. Only one adjusting wire 230 is shown for clarity. Locking ring 232 is positioned between proximal end 228 of adjustable section 210 and proximal end 208 of adjustable introducer sheath 204, and over adjusting wires 230. Locking ring 232 is configured to secure adjusting wires 230 from sliding, by radial inward force or other means, and thus keeping adjustable section 210 in an expanded state.

FIG. 17B illustrates the proximal coupler assembly 180 coupled to proximal end 208 of adjustable introducer sheath 204 shown in FIG. 17A. Locking ring 232 is expanded, or otherwise released, allowing adjusting wires 230 to slide proximally in direction 194 allowing adjustable section 210 to compress. Locking ring 232 may also be adapted with catches or clamps (not shown) to secure and then release adjustable wires 230.

Figure 18:
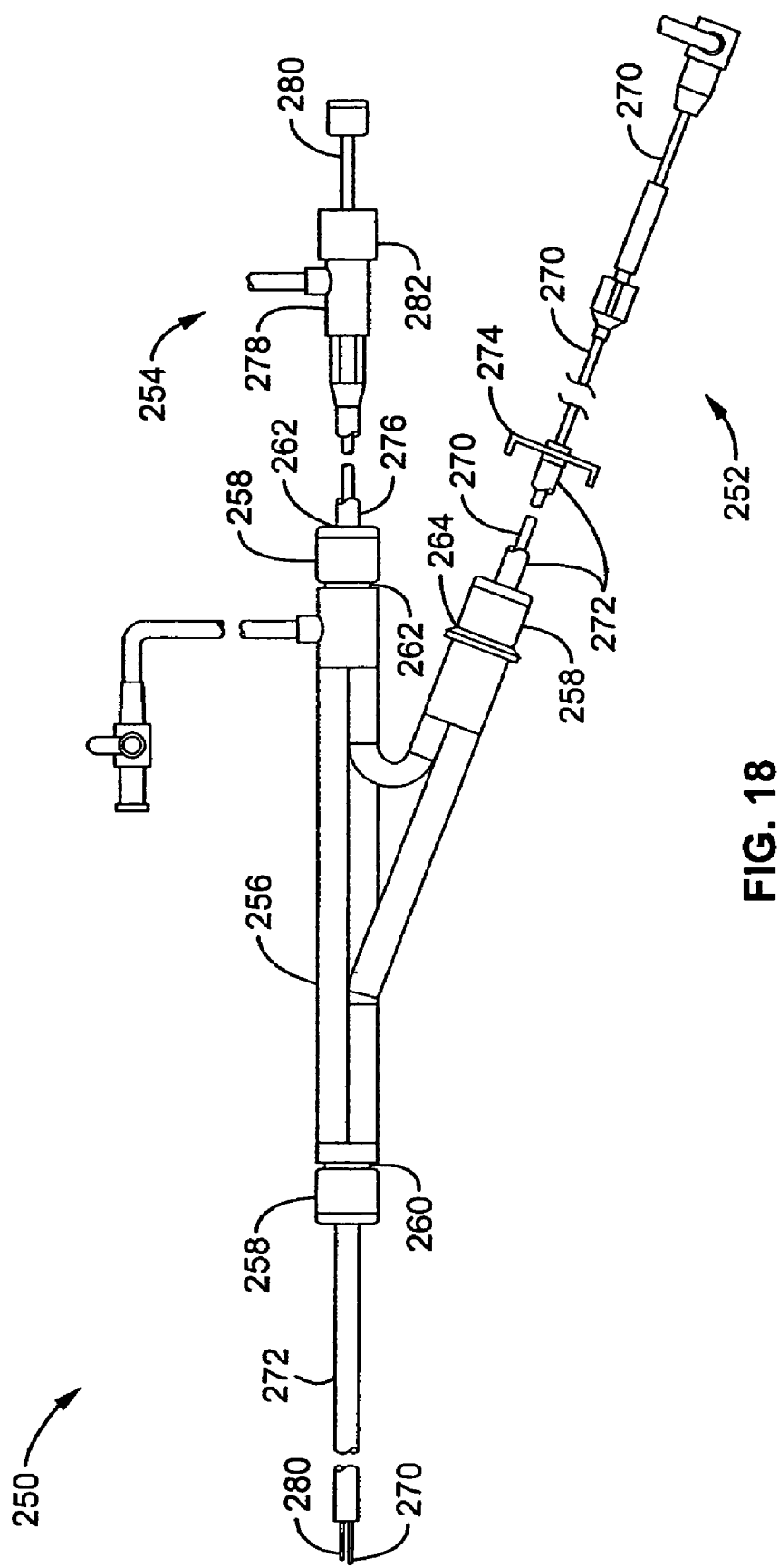
FIG. 18 is a stylized illustration of another embodiment of a proximal coupler system with a local fluid delivery system and a catheter assembly with a rigid tube.

FIG. 18 is a stylized illustration of another aspect of the invention with a proximal coupler assembly 250 coupled to a local fluid delivery system 252 and a catheter assembly 254. FIG. 19A and FIG. 19B further illustrate longitudinal cross sections of proximal coupler assembly 250. Proximal coupler assembly 250 comprises a Y hub body 256, similar to one shown in FIG. 2 to FIG. 5, with sealable adaptors 258 such as Touhy Borst valves, at the distal port 260, the proximal port 262 and secondary port 264. Y hub body 256 has main channel 266 (shown in FIG. 19A) connecting distal port 260 and proximal port 262 and secondary channel 268 (shown in FIG. 19A connecting secondary port 264 with main channel 266.

Local fluid delivery system 252 has a fluid agent infuser device 102 (shown in FIG. 13B), on the distal end of hypotube 270. Flexible delivery sheath 272 has a proximal handle 274. Flexible delivery sheath 272 encases the distal end and midsection of hypotube 270. The proximal end of hypotube 270 is configured for fluid delivery as previously shown in FIG. 10.

Catheter assembly 254 is similar to that previously shown in FIG. 1. A rigid tube 276 is coupled to catheter manifold 278 which is configured to receive catheter 280 and to couple to proximal coupler assembly 250 through proximal port 262 with rigid tube 276. Catheter 280 enters catheter manifold 278 through proximal port 260 and hemostasis valve 282. In one beneficial embodiment, catheter 280 is a guiding catheter about 6 Fr in diameter and about 100 cm in length.

In FIG. 18, flexible delivery sheath 272 is inserted in secondary port 264 through a sealable adapter 258 and advanced past distal port 260, into a position where the distal end of delivery sheath is proximal the renal arteries. Hypotube 270 of local fluid delivery system 252 is advanced distally until a fluid agent infuser device (shown in FIG. 13B) is in position near the renal arteries. Delivery sheath 272 is retracted through proximal coupler assembly 250 and secondary port 264 by pulling handle 274 to create an open transition zone proximal of a fluid agent infuser device as previously shown in FIG. 13B. In one beneficial mode, delivery sheath is retracted about 10 cm. The sealable adaptor 258 at secondary port 264 is tightened to hold delivery sheath 272 and hypotube 270 firmly in place.

In FIG. 19A, rigid tube 276 of catheter assembly 254 is inserted into proximal port 262 of proximal coupler assembly 250. Sealable valves 258 have been removed for clarity. Rigid tube 276 has pointed distal tip 284, which is advanced through proximal port 262 and into main channel 266.

In FIG. 19B pointed distal tip 284 of rigid tube 276 has advanced further distally and punctured delivery sheath 272 at the junction of main channel 266 and secondary channel 268. Distal tip 284 of rigid tube 276 is shown positioned within the inner lumen of delivery sheath 272 next to hypotube 270. Sealable adaptor 258 at proximal port 262 (shown in FIG. 18) is tightened to secure rigid tube 276 firmly in place. Catheter 280 is then advanced distally through hemostasis valve 282, catheter manifold 278 and rigid tube 276 (shown in FIG. 18), then through delivery sheath 272, and out the distal end of delivery sheath 272 for further medical intervention.

Figure 20:
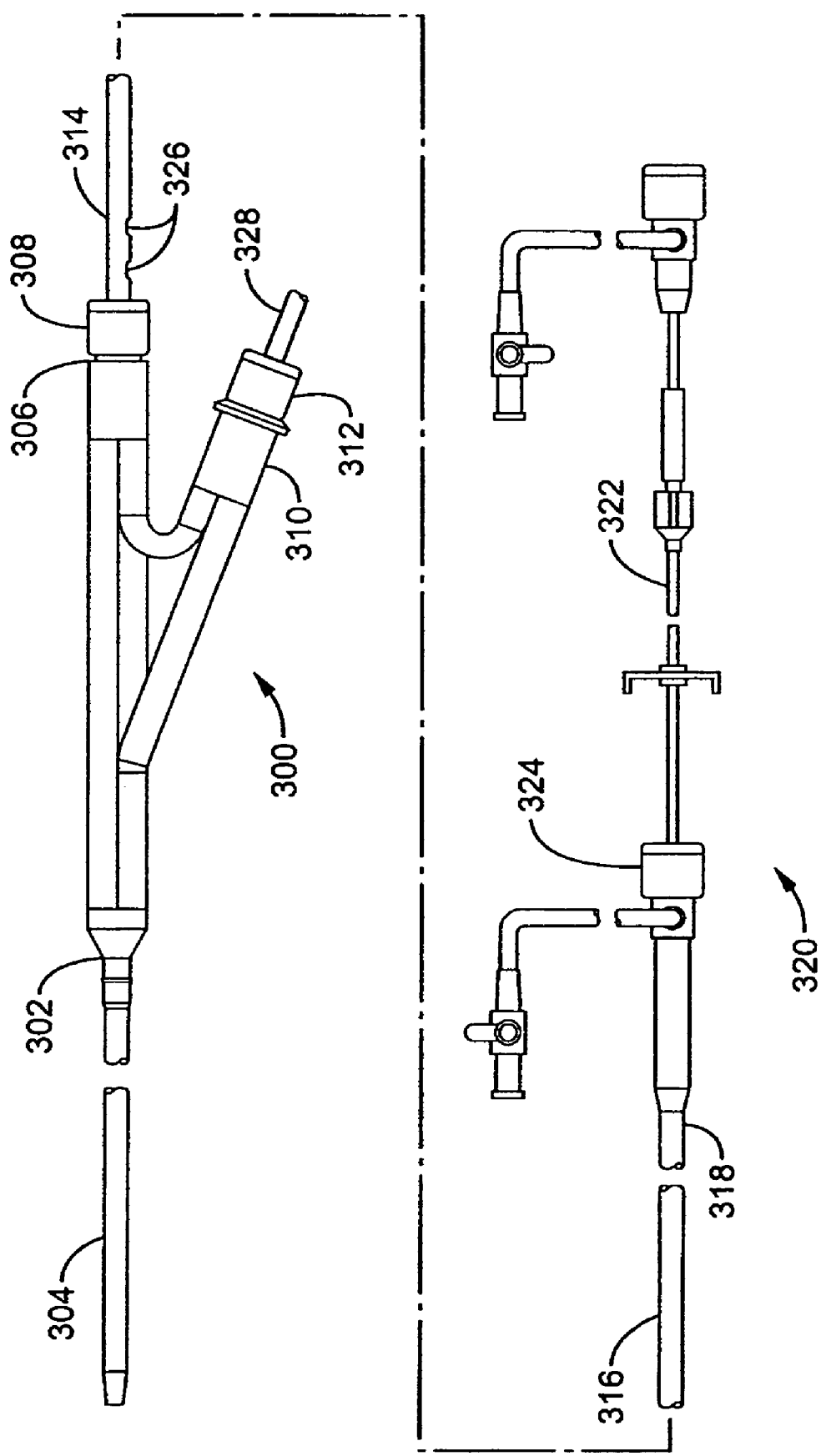
FIG. 20 illustrates another mode of inserting a catheter in a proximal coupler assembly through the secondary port using a delivery tube with precut holes.
Figure 21:
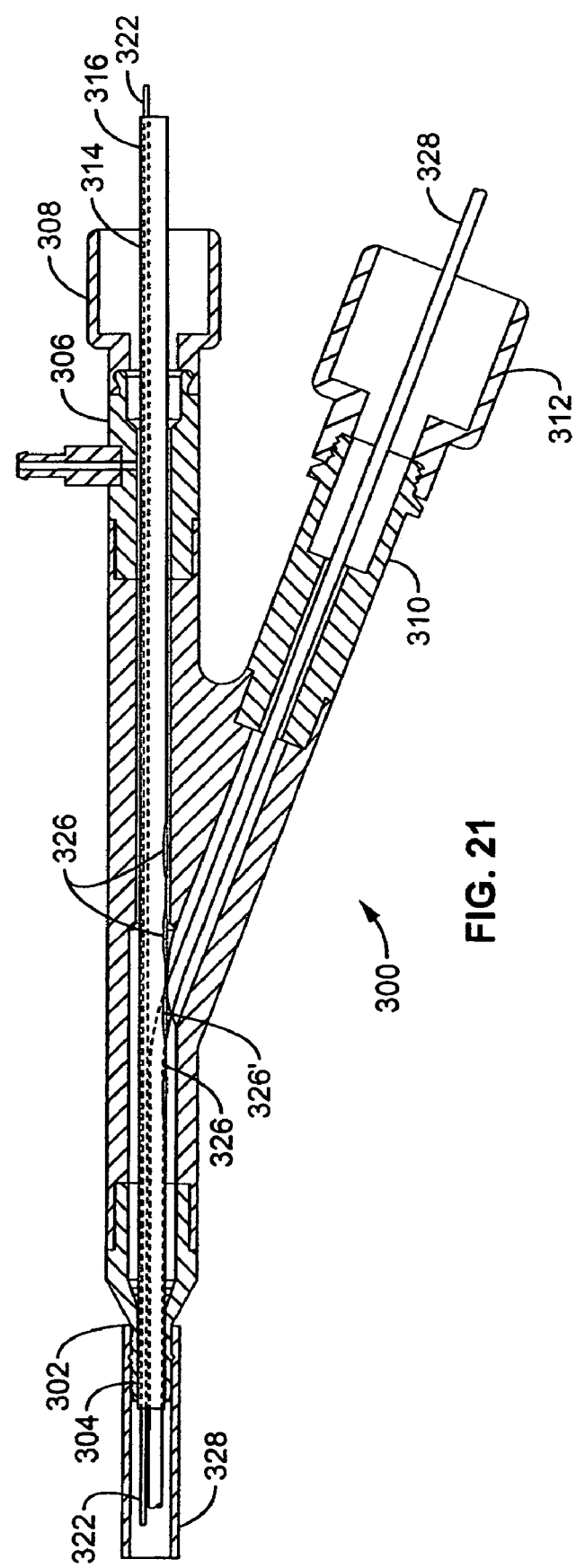
FIG. 21 is a cross-sectional view of FIG. 20 illustrating the hypotube advanced through the delivery sheath and guiding catheter entering through a precut hole in the delivery sheath.

FIG. 20 is a plan view and FIG. 21 is a cut away view of another mode of inserting a catheter adjacent a fluid delivery device wherein Y assembly 300 has distal end 302, coupled to introducer sheath 304, a proximal port 306 with hemostasis valve 308 and branch port 310 with a Touhy Borst valve 312 on said branch port. Proximal portion of delivery sheath 314, made from a stiff material such as stainless steel, having a proximal midsection 316 and a proximal end 318 is inserted in heomostasis valve 308 with distal end (not shown) in introducer sheath 304. Proximal end 318 of delivery sheath 314 is coupled to a local fluid delivery system 320, as previously described in FIG. 10. Further details of local fluid delivery system are omitted here for clarity. Hypotube 322 extending distally into delivery sheath 314 through Touhy Borst valve 324 on local fluid delivery system 320. Proximal midsection 316 of delivery sheath 314 has precut holes 326 spaced at predetermined intervals configured to accommodate a guiding catheter 328 introduced through branch port 310. In a preferred embodiment, guiding catheter 328 is about 100 cm long and about 6 Fr in diameter. Introducer sheath 304 is inserted in an aorta system as previously described in FIG. 13A. Deployment of a fluid agent infuser device as previously shown in FIG. 13B is accomplished by advancing delivery sheath 314 to the desired position and advancing hypotube 322 through delivery sheath 314 to position fluid agent infuser device 102. As previously shown in FIG. 13B, a fluid agent infuser device is deployed, delivery sheath 314 is retracted to form a transition zone, which in one embodiment, is about 10 cm. Y hub assembly 300 is advanced distally on the proximal portion of delivery sheath 314 until a preferred precut hole 326' (shown in FIG.21) is aligned with branch port 310 of Y hub assembly 300. Guiding catheter 328 is introduced through Touhy Borst valve 312 on branch port 310 and inserted through preferred hole 326' in delivery sheath 320.

Guiding catheter 328 is advanced distally through delivery sheath 314 along side hypotube 322 and finally to a target site as previously described in FIG. 13B. Y hub assembly 300 may be further modified by extending port 306 proximally to keep all precut holes 326 in delivery sheath 314 sealed inside Y hub assembly 300 and distal of hemostasis valve 308 during medical procedures.

Figure 22:
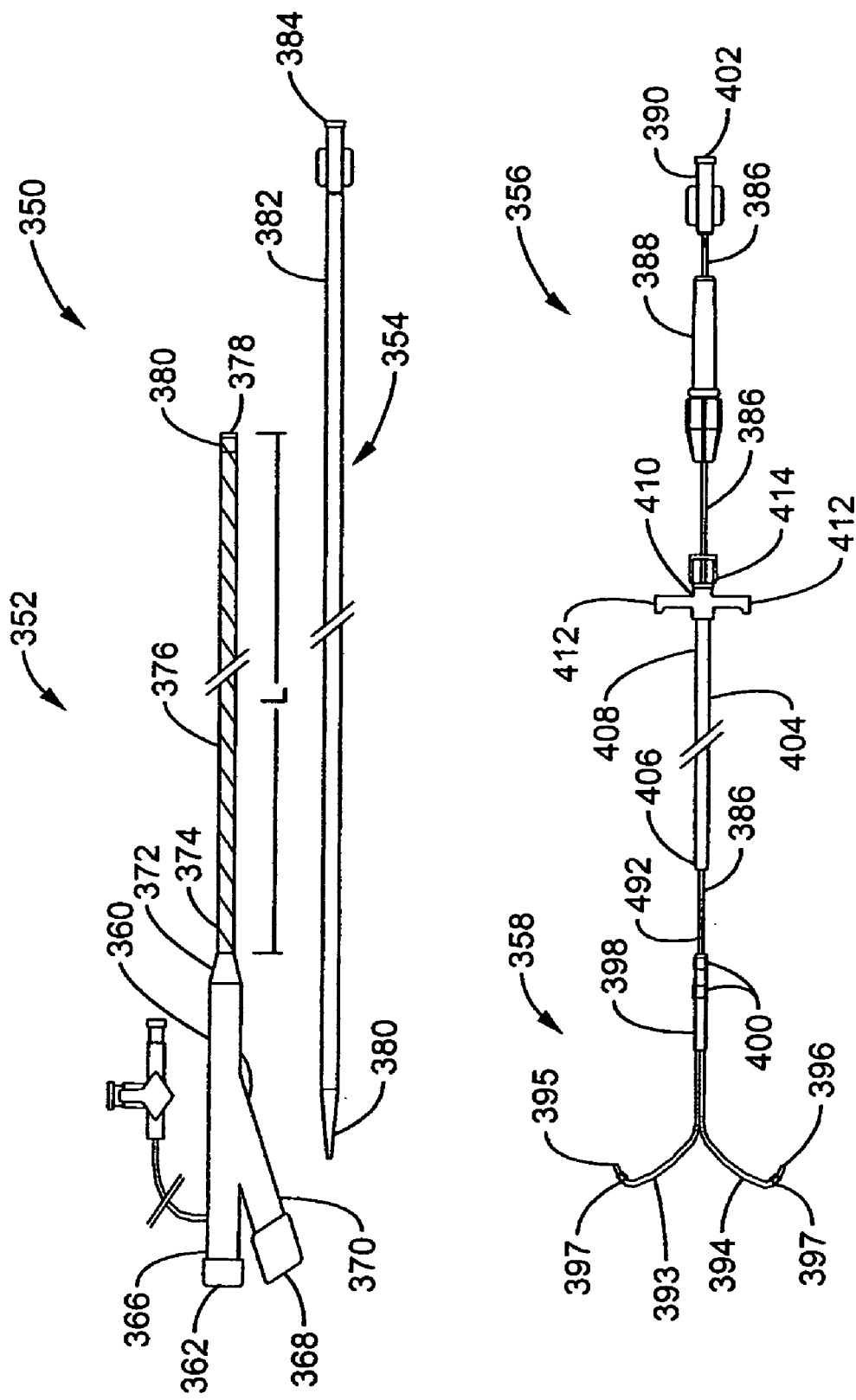
FIG. 22 illustrates a renal therapy system including an introducer sheath system, a vessel dilator and a fluid delivery system with a bifurcated renal catheter.

FIG. 22 illustrates a further embodiment of a proximal coupler assembly and a fluid delivery assembly as shown in FIG. 11B. Renal therapy system 350 includes an introducer sheath system 352, a vessel dilator 354, and a fluid delivery system 356 with a bifurcated renal catheter 358. Details of channels, saline systems and fittings as shown previously in FIG. 2 through FIG. 4 are omitted for clarity. Introducer sheath system 352 has Y hub body 360 as shown previously in FIG. 2 through FIG. 4 configured with various inner structures as shown previously in FIG. 3. Y hub body 360 has hemostasis valve 362 on proximal end 366 and Touhy Borst valve 368 on secondary end 370. Distal end 372 of Y hub body 360 is coupled to proximal end 374 of introducer sheath 376. Introducer sheath 376 has distal tip 378 that has a truncated cone shape and radiopaque marker band 380. In one embodiment, introducer sheath 376 is constructed with an inner liner of PTFE material, an inner coiled wire reinforcement, and an outer polymer jacket. Introducer sheath 376 has predetermined length L measured from proximal end 374 to distal tip 378.

Vessel dilator 354, with distal end 380 and proximal end 382 is a polymer, (e.g. extrusion) tubing with a center lumen for a guide wire (not shown). Distal end 380 is adapted with a taper cone shape. Proximal end 382 is coupled to a Luer fitting 384.

Fluid delivery system 356 has stiff tube 386, torque handle 388, and proximal hub 390 as previously described in FIG. 11A and FIG. 11B with bifurcated catheter 358 coupled at distal end 392. Bifurcated catheter 358 has two distal extensions 393, 394 of a memory shape material. Distal tips 395, 396 of each distal extension 393, 394 respectively, have a plurality of fluid ports (not shown) and radiopaque marker bands 397. Polymer tube 398 is positioned proximal of distal extensions 393 and 394 and have radiopaque marker bands 400. The proximal hub 390 of fluid delivery system 356 has a Luer fitting 402 for infusing a fluid agent, fluidly coupled with the stiff tube 386.

A single lumen, tear-away delivery sheath 404 has a distal end 406, a proximal end 408, and slidingly encases stiff tube 386. Delivery sheath 404 is positioned between the torque handle 388 and the bifurcated catheter 358. The distal end 406 has a shape and outer diameter adapted to mate with the channel restriction in the distal end of the main channel of the Y hub body as shown previously in FIG. 3. The proximal end 408 of the delivery sheath 404 is coupled to a handle assembly 410 with two handles 412 and a tear away cap 414.

Dilator 354 is inserted through Touhy Borst valve 368 on secondary port 370 until distal end 380 protrudes from distal tip 378 of introducer sheath 376 to form a smooth outer conical shape. Distal tip 378 of introducer sheath 376 is positioned in the aorta system near the renal arteries (not shown). Dilator 354 is removed and fluid delivery device 356 is prepared by sliding delivery sheath 404 distally until distal extensions 393 and 394 of bifurcated catheter 358 are enclosed in delivery sheath 404. Distal end 406 of delivery sheath 404 is inserted in Touhy Borst valve 368 and advanced to the restriction in the main channel of the Y hub body shown in FIG. 3. Bifurcated catheter 358 is advanced distally into introducer sheath 376. Tear away delivery sheath 404 is retracted and removed through Touhy Borst valve 368 as shown previously in FIG. 11B. Bifurcated catheter 358 is advanced distally out of the distal tip 378 of introducer sheath 376 and distal extensions 393 and 394 expand to their preformed shape to cannulate the renal arteries (not shown).

Notwithstanding the particular benefits provided by the various embodiments described above, one particular highly beneficial embodiment of an overall renal therapy system as shown previously in FIG. 22 is provided as follows in order to further illustrate certain aspects of the invention considered suitable for bi-lateral local renal delivery of therapeutic agents in many circumstances.

A Y hub body as shown previously in FIG. 2 through FIG. 4 is made of a clear material and is configured with a main channel and a secondary channel that intersects the main channel. The distal end of the main channel is adapted with a channel restriction as shown in FIG. 3. The Y hub body has an introducer sheath fitting at the distal end and a port for the introduction of a saline solution into the main channel of the Y hub body. A hemostasis valve is attached to the proximal fitting on the main branch of the Y hub body and is configured to accommodate a nominal 6 French diameter catheter. A Touhy Borst valve is attached to the secondary fitting on the secondary port of the Y hub body.

An introducer sheath is coupled to the introducer sheath fitting of the Y hub body and is constructed with an inner liner of TFE material; an inner-coiled wire reinforcement, and an outer polymer jacket. The nominally 8 French introducer sheath has an inner diameter of about 0.116 inches and an outer diameter of about 0.138 inches. The distal tip is shaped as a truncated cone to adapt with the distal tip of a vessel dilator and has a radiopaque marker band. The proximal end of the introducer sheath is comprised of the outer polymer jacket only and is flared to couple to the introducer sheath fitting on the Y hub body. In one highly beneficial embodiment, multiple introducer sheaths are provided with a renal therapy system to accommodate different anatomies. Introducer sheaths with nominal usable lengths L, as shown in FIG. 22, of about 30 cm, about 35 cm, about 40 cm, and about 45 cm are typically included, but other suitable lengths can be provided as well. In the present example, the different length introducer sheaths are each coupled to a Y body hub as an integrated introducer sheath system; however, the system may be packaged and sold separately for later assembly.

A vessel dilator is used with this renal therapy system to guide the distal tip of the introducer sheath to the proximal region of the renal arteries. The vessel dilator is a polymer extrusion, tapered at the distal end with an inner lumen of about 0.040 inches and adapted for passage of a guide wire of about 0.035 inches to about 0.038 inches in diameter. The vessel dilator length is nominally about 11 cm longer than the usable length of the corresponding introducer sheath used so as to extend from the distal tip of the sheath and also out the appropriate proximal port of the Y hub body. The proximal end of the vessel dilator has a Luer fitting, primarily for flushing the inner lumen with a saline solution.

After the position of the renal arteries relative to the percutaneous entry point has been established using a guide wire with a diagnostic catheter and methods known to exist in the art, an integrated introducer sheath system of suitable length is selected. The vessel dilator is introduced through the Touhy Borst valve on the secondary branch of the Y hub and advanced until the distal tip of the vessel dilator protrudes from the distal tip of the introducer sheath resulting in a smooth outer conical shape. A saline flush is introduced through the port on the Y body and the proximal port of the vessel dilator. The introducer sheath with vessel dilator inserted is advanced on the guide wire through the percutaneous entry point and to the region in the aorta of the renal arteries. The marker band on the distal tip of the introducer sheath may be used with fluoroscopy to aid in positioning. When the distal tip of the introducer sheath is positioned at or near the renal arteries, the vessel dilator and guide wire are retracted, and removed, from the Y hub body through the Touhy Borst valve, while the introducer sheath remains in place.

A fluid delivery system as previously shown in FIG. 11A is prepared for insertion into the Y hub body. In this embodiment, the fluid delivery system has a stiff tube preferably made of Nitinol tubing and is about 77 cm in usable length with a distal end, a mid proximal portion and a proximal end. A bifurcated catheter is coupled at the distal end of the stiff tube. The distal extensions of the bifurcated catheter have a memory shape and are made of a braid-reinforced polymer with an inner core of ribbon wire. Each distal extension in this example has a radiopaque marker band and two infusion ports at or near the distal tip. The outside diameter of each of the distal extensions is nominally about 3 French. There is a polymer tube encasing the bifurcated catheter in a position proximal of the union of the distal extensions. The polymer tube has two radiopaque markers positioned about 1 cm to about 1.5 cm proximal of the union of the distal extensions to aid in relative positioning of the bifurcated catheter and the introducer sheath.

The fluid delivery system has a torque handle coupled at the mid proximal portion of the stiff tube and a proximal hub coupled at the proximal end of the stiff tube. The proximal hub has a Luer fitting for infusing a fluid agent and a saline flush port fluidly coupled with the stiff tube.

A single lumen, tear-away delivery sheath slidingly encases the stiff tube and is positioned between the torque handle and the bifurcated catheter. The delivery sheath is nominally about 15 cm in length with a distal end and a proximal end. The distal end has a shape and outer diameter adapted to mate with the channel restriction in the distal end of the main channel of the Y hub body as shown previously in FIG. 3. The proximal end of the delivery sheath is coupled to a handle assembly with two handles. The handle assembly has a tear away cap on the proximal end and is configured to allow the handle assembly to separate into two portions when the tear-away cap is removed and the handles pulled apart. The circumferential profile of the delivery sheath is configured with opposing thin wall sections to facilitate splitting lengthwise in two pieces when the handles are pulled apart.

The fluid delivery system is prepared by flushing saline solution from the saline port in the stiff tube proximal hub through to infusion ports in the distal extension tips of the bifurcated catheter. The bifurcated catheter is loaded into the delivery sheath by pulling the catheter relative to the delivery sheath handle until the tips of the distal extensions of the bifurcated catheter are completely within the delivery sheath.

The distal end of the delivery sheath, with the bifurcated catheter loaded, is inserted through the Touhy Borst valve on the secondary port of the Y hub body until the distal end seats in the channel restriction in the main channel. Distal force on the torque handle of the stiff tube advances the bifurcated catheter into the introducer sheath, preferably at least about 15 cm (about the length of the tear away delivery sheath) into introducer sheath to ensure the distal extensions are completely out of the tear away delivery sheath and into the introducer sheath.

The tear away delivery sheath is retracted from the Y hub body by pulling in a proximal position on the delivery sheath handle assembly as previously described in FIG. 11B. During the delivery sheath retraction, the bifurcated catheter remains in position in the introducer sheath. When the distal end of the delivery sheath is removed from the Y hub body, the Touhy Borst valve is tightened on the stiff tube to prevent fluid loss. The tear away cap is removed from the delivery sheath handle assembly and the handles are pulled apart, tearing the delivery sheath longitudinally and into two pieces, which are removed from the stiff tube and discarded.

The bifurcated catheter is advanced to the distal tip of the introducer sheath by distal movement of the stiff tube at the torque handle relative to the Y hub body. Using fluoroscopic guidance, the bifurcated catheter is advanced out of the distal tip of the introducer sheath. The bifurcated catheter is manipulated through the torque handle, and the introducer sheath is simultaneously retracted, and the distal extensions bias toward their memory shape in the aorta and cannulate the renal arteries. Once the distal extensions are completely extended out of the distal tip of the introducer sheath and positioned in the renal arteries, the distal tip of the introducer sheath is retracted at least just proximal of the marker bands on the polymer tube of the bifurcated catheter to allow for interventional catheter advancement, while the bifurcated catheter remains in place. With the introducer sheath positioned, the Touhy Borst valve is tightened to prevent further movement of the bifurcated catheter in the introducer sheath.

The introducer sheath may be sutured or otherwise positionally controlled at or near the percutaneous entry site to prevent sheath movement during the subsequent procedure. Fluid agent may now be delivered through the proximal port of the fluid delivery system, through the stiff tube and into the renal arteries through the bifurcated catheter similar to that shown in FIG. 22

Medical intervention procedures, such as coronary procedures, are initiated by inserting the appropriate guide wires and catheters through the hemostasis valve on the proximal fitting of the Y hub body. In this example, a nominal 6 French catheter will advance through the introducer sheath and along side the stiff tube without significant resistance.

When medical interventions are complete, the intervention catheters and guide wires are retracted and removed from the Y hub body through the hemostasis valve. Fluid agent delivery is often stopped. The Touhy Borst valve is loosened and torque handle of the stiff tube is pulled proximally relative to the Y hub body, withdrawing the distal extensions of the bifurcated catheter out of the renal arteries and into the introducer sheath. The introducer sheath is retracted from the percutaneous entry point and the entry point closed with standard medical procedures.

The various embodiments herein described for the present invention can be useful in treatments and therapies directed at the kidneys such as the prevention of radiocontrast nephropathy (RCN) arising from diagnostic procedures using iodinated contrast materials. As a prophylactic treatment method for patients undergoing interventional procedures that have been identified as being at elevated risk for developing RCN, a series of treatment schemes have been developed based upon local therapeutic agent delivery to the kidneys. Among the agents identified for such treatment are normal saline (NS) and the vasodilators papaverine (PAP) and fenoldopam mesylate (FM).

The approved use for fenoldopam is for the in-hospital intravenous treatment of hypertension when rapid, but quickly reversible, blood pressure lowering is needed. Fenoldopam causes dose-dependent renal vasodilation at systemic doses as low as approximately 0.01 mcg/kg/min through approximately 0.5 mcg/kg/min IV and it increases blood flow both to the renal cortex and to the renal medulla. Due to this physiology, fenoldopam may be utilized for protection of the kidneys from ischemic insults such as high-risk surgical procedures and contrast nephropathy. Dosing from approximately 0.01 to approximately 3.2 mcg/kg/min is considered suitable for most applications of the present embodiments, or about 0.005 to about 1.6 mcg/kg/min per renal artery (or per kidney). As before, it is likely beneficial in many instances to pick a starting dose and titrate up or down as required to determine a patient's maximum tolerated systemic dose. Recent data, however, suggest that about 0.2 mcg/kg/min of fenoldopam has greater efficacy than about 0.1 mcg/kg/min in preventing contrast nephropathy and this dose is preferred.

The dose level of normal saline delivered bilaterally to the renal arteries may be set empirically, or beneficially customized such that it is determined by titration. The catheter or infusion pump design may provide practical limitations to the amount of fluid that can be delivered; however, it would be desired to give as much as possible, and is contemplated that levels up to about 2 liters per hour (about 25 cc/kg/hr in an average about 180 lb patient) or about one liter or 12.5 cc/kg per hour per kidney may be beneficial.

Local dosing of papaverine of up to about 4 mg/min through the bilateral catheter, or up to about 2 mg/min has been demonstrated safety in animal studies, and local renal doses to the catheter of about 2 mg/min and about 3 mg/min have been shown to increase renal blood flow rates in human subjects, or about 1 mg/min to about 1.5 mg/min per artery or kidney. It is thus believed that local bilateral renal delivery of papaverine will help to reduce the risk of RCN in patients with pre-existing risk factors such as high baseline serum creatinine, diabetes mellitus, or other demonstration of compromised kidney function.

It is also contemplated according to further embodiments that a very low, systemic dose of papaverine may be given, either alone or in conjunction with other medical management such as for example saline loading, prior to the anticipated contrast insult. Such a dose may be on the order for example of between about 3 to about 14 mg/hr (based on bolus indications of approximately 10–40 mg about every 3 hours—papaverine is not generally dosed by weight). In an alternative embodiment, a dosing of 2–3 mg/min or 120–180 mg/hr. Again, in the context of local bilateral delivery, these are considered halved regarding the dose rates for each artery itself.

Notwithstanding the particular benefit of this dosing range for each of the aforementioned compounds, it is also believed that higher doses delivered locally would be safe. Titration is a further mechanism believed to provide the ability to test for tolerance to higher doses. In addition, it is contemplated that the described therapeutic doses can be delivered alone or in conjunction with systemic treatments such as intraveneous saline.

It is to be understood that the invention can be practiced in other embodiments that may be highly beneficial and provide certain advantages. For example radiopaque markers are shown and described above for use with fluoroscopy to manipulate and position the introducer sheath and the intra renal catheters. The required fluoroscopy equipment and auxiliary equipment devices are typically located in a specialized location limiting the in vivo use of the invention to that location. Other modalities for positioning intra renal catheters are highly beneficial to overcome limitations of fluoroscopy. For example, non fluoroscopy guided technology is highly beneficial for use in operating rooms, intensive care units, and emergency rooms, where fluoroscopy may not be readily available or its use may cause undue radiation exposure to users and others due to a lack of specific radiation safeguards normally present in angiography suites and the like. The use of non-fluoroscopy positioning allows intra renal catheter systems and methods to be used to treat other diseases such as ATN and CHF in clinical settings outside of the angiography suite or catheter lab.

In one embodiment, the intra renal catheter is modified to incorporate marker bands with metals that are visible with ultrasound technology. The ultrasonic sensors are placed outside the body surface to obtain a view. In one variation, a portable, noninvasive ultrasound instrument is placed on the surface of the body and moved around to locate the device and location of both renal ostia. This technology is used to view the aorta, both renal ostia and the intra renal catheter.

In another beneficial embodiment, ultrasound sensors are placed on the introducer sheath and the intra renal catheter itself; specifically the tip of the distal extensions, along the distal extensions or at the distal end of the catheter. The intra renal catheter with the ultrasonic sensors implemented allows the physician to move the sensors up and down the aorta to locate both renal ostia.

A further embodiment incorporates Doppler ultrasonography with the intra renal catheters. Doppler ultrasonography detects the direction, velocity, and turbulence of blood flow. Since the renal arteries are isolated along the aorta, the resulting velocity and turbulence is used to locate both renal ostia. A further advantage of Doppler ultrasongraphy is it is non invasive and uses no x rays.

A still further embodiment incorporates optical technology with the intra renal catheter. An optical sensor is placed at the tip of the introducer sheath. The introducer sheath's optical sensor allows visualization of the area around the tip of the introducer sheath to locate the renal ostia. In a further mode of this embodiment, a transparent balloon is positioned around the distal tip of the introducer sheath. The balloon is inflated to allow optical visual confirmation of renal ostium. The balloon allows for distance between the tip of the introducer sheath and optic sensor while separating aorta blood flow. That distance enhances the ability to visualize the image within the aorta. In a further mode, the balloon is adapted to allow profusion through the balloon wall while maintaining contact with the aorta wall. An advantage of allowing wall contact is the balloon can be inflated near the renal ostium to be visually seen with the optic sensor. In another mode, the optic sensor is placed at the distal tips of the intra renal catheter. Once the intra renal catheter is deployed within the aorta, the optic sensor allows visual confirmation of the walls of the aorta. The intra renal catheter is tracked up and down the aorta until visual confirmation of the renal ostia is found. With the optic image provided by this mode, the physician can then track the intra renal catheter into the renal arteries to a predetermined depth.

Another embodiment uses sensors that measure pressure, velocity, and/or flow rate to locate renal ostia without the requirement of fluoroscopy equipment. The sensors are positioned at the tip of distal extensions of the intra renal catheter. The sensors display real time data about the pressure, velocity, and/or flow rate. With the real-time data provided, the physician locates both renal ostia by observing the sensor data when the intra renal catheter is around the approximate location of the renal ostia. In a further mode of this embodiment, the intra renal catheter has multiple sensors positioned at a mid distal and a mid proximal position on the catheter to obtain mid proximal and mid distal sensor data. From this real time data, the physician can observe a significant flow rate differential above and below the renal arteries and locate the approximate location. With the renal arteries being the only significant sized vessels within the region, the sensors would detect significant changes in any of the sensor parameters.

In a still further embodiment, chemical sensors are positioned on the intra renal catheter to detect any change in blood chemistry that indicates to the physician the location of the renal ostia. Chemical sensors are positioned at multiple locations on the intra renal catheter to detect chemical change from one sensor location to another.

Additional modifications or improvements may be made by the embodiments shown and described herein without departing from the intended scope of the invention which is considered to be broadly beneficial according to various independent aspects described. For example, various modifications to or combinations with the present embodiments may be made in view of other available information to one of ordinary skill in the art upon review of this disclosure and remain within the intended scope of the invention.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A local renal therapy system, comprising:
an introducer sheath with a tubular wall with a proximal end portion, a distal end portion that is adapted to be positioned at a location within an abdominal aorta associated with first and second renal ostia of first and second renal arteries, respectively, while the proximal end portion extends externally from the patient, and an introducer lumen that extends along a longitudinal axis between a proximal port along the proximal end portion and a distal port along the distal end portion;
a bilateral renal delivery assembly with a local injection assembly that is adapted to be delivered to the location in a first condition through the introducer lumen;
wherein the introducer sheath has an adjustable length between a first configuration and a second configuration;
wherein in the first configuration the introducer sheath has a first length that is adapted to deliver the local injection assembly in a first condition to the location;
wherein in the second configuration the introducer sheath has a second length that is shorter than the first length and that corresponds with the local injection assembly extending in a second condition distally from the distal port at the location; and
wherein in the second condition at the location the local injection assembly is adapted to be coupled to a source of fluid agent externally of the patient and to deliver a volume of fluid from the source bilaterally into each of the two renal arteries.

2. The system of claim 1, wherein:
the tubular wall has an adjustable section with an accordion shape with a series of undulations along a length;
wherein in the first configuration the accordion shape has a first shape with a first length and a first amplitude of the undulations transverse to the longitudinal axis;
wherein in the second configuration the accordion shape has a second length that is shorter than the first length and a second amplitude that is greater than the first amplitude.

3. The system of claim 2, further comprising:
an adjustable member that is coupled to the tubular wall and is adjustable between a first position along the tubular wall relative to the adjustable section and a second position along the tubular wall relative to the adjustable section;
wherein the first position corresponds with the first configuration for the introducer sheath and is located to coincide with the adjustable section so as to limit the undulations to the first amplitude and thus expand the adjustable section to the first length;
wherein the second position corresponds with the second configuration for the introducer sheath and is longitudinally removed from the adjustable section; and
wherein the second shape is a memory shape for the adjustable section.

4. The system of claim 3, wherein the adjustable member is located within the introducer lumen.

5. The system of claim 3, wherein the adjustable member is located externally around the tubular wall and is adapted to radially confine the adjustable section to the first shape in the first position.

* * * * *